United States Patent
Mahmoudi

(10) Patent No.: US 12,290,310 B2
(45) Date of Patent: May 6, 2025

(54) SLICING ELEMENTS FOR SHUNTING CATHETERS

(71) Applicant: THERAHEART INC., Irvine, CA (US)

(72) Inventor: Rani Abdullah Mahmoudi, Huntington Beach, CA (US)

(73) Assignee: Theraheart Inc., Irvine, CA (US)

( * ) Notice: Subject to any disclaimer, the term of this patent is extended or adjusted under 35 U.S.C. 154(b) by 0 days.

(21) Appl. No.: 18/628,225

(22) Filed: Apr. 5, 2024

(65) Prior Publication Data

US 2024/0335228 A1    Oct. 10, 2024

Related U.S. Application Data

(60) Provisional application No. 63/457,663, filed on Apr. 6, 2023.

(51) Int. Cl.
| | | |
|---|---|---|
| *A61B 18/14* | (2006.01) | |
| *A61B 17/32* | (2006.01) | |
| *A61B 17/34* | (2006.01) | |
| *A61B 18/18* | (2006.01) | |
| *A61B 18/24* | (2006.01) | |

(Continued)

(52) U.S. Cl.
CPC .. *A61B 18/1492* (2013.01); *A61B 17/320068* (2013.01); *A61B 17/3496* (2013.01); *A61B 18/1815* (2013.01); *A61B 18/24* (2013.01); *A61B 2017/00778* (2013.01); *A61B 2017/320074* (2017.08); *A61B 2018/00386* (2013.01); *A61B 2018/00577* (2013.01); *A61B 2018/00982* (2013.01);

(Continued)

(58) Field of Classification Search
CPC ........ A61B 18/1492; A61B 17/320068; A61B 17/3496; A61B 18/1815; A61B 18/24; A61B 2017/320074; A61B 2017/00778; A61B 2018/00386; A61B 2018/00577; A61B 2018/00982; A61B 2018/1861; A61M 25/0012; A61M 25/005
See application file for complete search history.

(56) References Cited

U.S. PATENT DOCUMENTS

| | | | |
|---|---|---|---|
| 4,861,336 A | 8/1989 | Helzel | |
| 5,255,679 A | 10/1993 | Imran | |

(Continued)

FOREIGN PATENT DOCUMENTS

| | | | | |
|---|---|---|---|---|
| AU | 2015237719 A1 | * | 11/2015 | ..... A61B 17/320016 |
| CA | 2472701 C | | 11/2012 | |

(Continued)

OTHER PUBLICATIONS

Patent Cooperative Treaty, International Search Report, mailed Jul. 17, 2024, in PCT/US2024/022547.

(Continued)

*Primary Examiner* — Aaron F Roane

(74) *Attorney, Agent, or Firm* — Faegre Drinker Biddle & Reath LLP

(57) ABSTRACT

At least some embodiments of the present disclosure are directed to systems, apparatus, and methods for creating a shunt in a patient. In some embodiments, a shunting catheter includes a catheter shaft including a shaft lumen and a slicing element. In certain embodiments, the slicing element includes a slicing element shaft, a puncture element, and a slicer.

27 Claims, 14 Drawing Sheets

(51) Int. Cl.
*A61B 17/00* (2006.01)
*A61B 18/00* (2006.01)
*A61M 25/00* (2006.01)

(52) U.S. Cl.
CPC .. *A61B 2018/1861* (2013.01); *A61M 25/0012* (2013.01); *A61M 25/005* (2013.01)

(56) References Cited

U.S. PATENT DOCUMENTS

| | | | |
|---|---|---|---|
| 5,328,472 A | 7/1994 | Rupp et al. | |
| 5,800,450 A | 9/1998 | Lary et al. | |
| 6,179,832 B1 | 1/2001 | Tartaglia et al. | |
| 6,726,677 B1 | 4/2004 | Flaherty et al. | |
| 7,018,400 B2 | 3/2006 | Haarstad et al. | |
| 7,150,745 B2 | 12/2006 | Stern et al. | |
| 7,655,005 B2 | 2/2010 | Bhola | |
| 7,674,256 B2 | 3/2010 | Marrouche et al. | |
| 7,966,057 B2 | 6/2011 | Macaulay et al. | |
| 8,021,359 B2 | 9/2011 | Auth et al. | |
| 8,043,360 B2 | 10/2011 | McNamara et al. | |
| 8,157,860 B2 | 4/2012 | McNamara et al. | |
| 8,172,896 B2 | 5/2012 | McNamara et al. | |
| 8,214,015 B2 | 7/2012 | Macaulay et al. | |
| 8,226,619 B2 | 7/2012 | Smith et al. | |
| 8,252,042 B2 | 8/2012 | McNamara et al. | |
| 8,374,680 B2 | 2/2013 | Thompson | |
| 8,585,596 B1 | 11/2013 | Flaherty et al. | |
| 8,617,152 B2 | 12/2013 | Flaherty et al. | |
| 8,728,073 B2 | 5/2014 | McDaniel | |
| 8,758,363 B2 | 6/2014 | Nishtala et al. | |
| 8,874,237 B2 | 10/2014 | Schilling | |
| 8,882,697 B2 | 11/2014 | McNamara et al. | |
| 8,900,250 B2 | 12/2014 | Fritscher-Ravens et al. | |
| 8,926,602 B2 | 1/2015 | Pageard | |
| 8,968,233 B2 | 3/2015 | Duffy et al. | |
| 9,089,314 B2 | 7/2015 | Wittenberger | |
| 9,345,858 B2 | 5/2016 | Flaherty et al. | |
| 9,468,744 B2 | 10/2016 | Arana et al. | |
| 9,642,993 B2 | 5/2017 | McNamara et al. | |
| 9,789,294 B2 | 10/2017 | Taft et al. | |
| 9,808,303 B2 | 11/2017 | Gelfand et al. | |
| 9,808,304 B2 | 11/2017 | Lalonde | |
| 9,814,483 B2 | 11/2017 | Vardi | |
| 9,918,789 B2 | 3/2018 | Bagley et al. | |
| 10,016,620 B2 | 7/2018 | Aljuri et al. | |
| 10,039,905 B1 | 8/2018 | Taft et al. | |
| 10,154,878 B2 | 12/2018 | Greenlaw et al. | |
| 10,188,375 B2 | 1/2019 | McNamara et al. | |
| 10,207,126 B2 | 2/2019 | Benson | |
| 10,245,352 B2 | 4/2019 | Wilson et al. | |
| 10,327,791 B2 | 6/2019 | Argentine et al. | |
| 10,426,497 B2 | 10/2019 | Chou et al. | |
| 10,449,339 B2 | 10/2019 | Wilson et al. | |
| 10,568,688 B2 | 2/2020 | Hu et al. | |
| 10,568,751 B2 | 2/2020 | McNamara | |
| 10,624,621 B2 | 4/2020 | Celermajer | |
| 10,639,060 B2 | 5/2020 | Vardi et al. | |
| 10,722,300 B2 | 7/2020 | Gupta et al. | |
| 10,729,492 B2 | 8/2020 | Brown et al. | |
| 10,758,714 B2 | 9/2020 | Laby et al. | |
| 10,842,562 B2 | 11/2020 | Zhang et al. | |
| 10,857,328 B2 | 12/2020 | Walzman | |
| 10,864,041 B2 | 12/2020 | Urbanski et al. | |
| 10,932,723 B2 | 3/2021 | Eliason et al. | |
| 10,980,552 B2 | 4/2021 | Mustapha | |
| 10,987,494 B2 | 4/2021 | Skinner et al. | |
| 10,993,735 B2 | 5/2021 | Vardi et al. | |
| 10,993,736 B2 | 5/2021 | Vardi et al. | |
| 11,052,246 B2 | 7/2021 | Stewart et al. | |
| 11,065,019 B1 | 7/2021 | Chou et al. | |
| 11,071,585 B2 | 7/2021 | Zhang et al. | |
| 11,083,520 B2 | 8/2021 | Ghaly et al. | |
| 11,135,410 B2 | 10/2021 | Finch et al. | |
| 11,224,449 B2 | 1/2022 | Chou et al. | |
| 11,224,450 B2 | 1/2022 | Chou et al. | |
| 11,350,990 B2 | 6/2022 | Gupta et al. | |
| 11,369,346 B2 | 6/2022 | Stigall et al. | |
| 11,369,405 B2 | 6/2022 | Vardi et al. | |
| 11,399,852 B2 | 8/2022 | Wilson et al. | |
| 11,534,239 B2 | 12/2022 | Bishara et al. | |
| 11,612,432 B2 | 3/2023 | Pate et al. | |
| 11,648,042 B2 | 5/2023 | Kelley | |
| 11,690,609 B2 | 7/2023 | Celermajer | |
| 11,717,429 B2 | 8/2023 | Schwartz et al. | |
| 11,752,314 B2 | 9/2023 | Taft et al. | |
| 11,793,529 B2 | 10/2023 | Chou et al. | |
| 11,806,032 B2 | 11/2023 | Chou et al. | |
| 11,865,282 B2 | 1/2024 | Nae et al. | |
| 11,957,374 B2 | 4/2024 | Vardi et al. | |
| 12,004,802 B2 | 6/2024 | Scott et al. | |
| 2005/0154386 A1 | 7/2005 | West et al. | |
| 2005/0171527 A1 | 8/2005 | Bhola | |
| 2006/0135961 A1 | 6/2006 | Rosenman et al. | |
| 2007/0083194 A1 | 4/2007 | Kunis et al. | |
| 2009/0125097 A1 | 5/2009 | Bruszewski et al. | |
| 2012/0123466 A1 | 5/2012 | Porter et al. | |
| 2012/0130417 A1 | 5/2012 | Lepulu et al. | |
| 2014/0277054 A1 | 9/2014 | McNamara et al. | |
| 2015/0209526 A1 | 7/2015 | Matsubara et al. | |
| 2016/0175041 A1 | 6/2016 | Govari et al. | |
| 2016/0206851 A1* | 7/2016 | Bannister | A61M 37/00 |
| 2018/0236211 A1 | 8/2018 | Henschel | |
| 2019/0374254 A1 | 12/2019 | Arevalos et al. | |
| 2020/0030588 A1 | 1/2020 | Heilman et al. | |
| 2020/0038672 A1 | 2/2020 | Satake | |
| 2020/0170662 A1 | 6/2020 | Vardi et al. | |
| 2020/0238059 A1 | 7/2020 | Wang et al. | |
| 2020/0261704 A1 | 8/2020 | Wang et al. | |
| 2020/0367924 A1 | 11/2020 | Lenker et al. | |
| 2021/0038298 A1 | 2/2021 | Scott et al. | |
| 2021/0045805 A1 | 2/2021 | Govari et al. | |
| 2021/0085384 A1 | 3/2021 | Morey et al. | |
| 2021/0196373 A1 | 7/2021 | He et al. | |
| 2021/0228227 A1 | 7/2021 | Vardi et al. | |
| 2021/0315629 A1 | 10/2021 | Yang et al. | |
| 2021/0369321 A1 | 12/2021 | Yang et al. | |
| 2021/0393324 A1 | 12/2021 | Moriyama et al. | |
| 2022/0022954 A1 | 1/2022 | Shuros et al. | |
| 2022/0110679 A1 | 4/2022 | Wang et al. | |
| 2022/0249160 A1 | 8/2022 | Pate et al. | |
| 2022/0257318 A1 | 8/2022 | Belalcazar | |
| 2022/0265346 A1 | 8/2022 | Gupta et al. | |
| 2022/0273279 A1 | 9/2022 | Valdez et al. | |
| 2022/0330975 A1 | 10/2022 | Rafiee et al. | |
| 2023/0041021 A1 | 2/2023 | Urbanski et al. | |
| 2023/0078647 A1 | 3/2023 | Sharma et al. | |
| 2023/0099410 A1 | 3/2023 | Primeaux | |
| 2023/0210592 A1 | 7/2023 | Agnew et al. | |
| 2023/0248425 A1 | 8/2023 | Iijima | |
| 2023/0270491 A1 | 8/2023 | Mori et al. | |
| 2023/0293877 A1 | 9/2023 | Hoem | |
| 2024/0050717 A1 | 2/2024 | Rickerson et al. | |

FOREIGN PATENT DOCUMENTS

| | | | | |
|---|---|---|---|---|
| CN | 109965974 A | 7/2019 | | |
| CN | 115475001 A | 12/2022 | | |
| CN | 115590605 A | 1/2023 | | |
| EP | 1878453 B1 | 12/2014 | | |
| EP | 3238646 A2 | 11/2017 | | |
| EP | 3705154 A1 | 9/2020 | | |
| JP | 5237572 B2 | 7/2013 | | |
| WO | 2003/049643 A1 | 6/2003 | | |
| WO | 2018/229768 A2 | 12/2018 | | |
| WO | 2018/229768 A9 | 12/2018 | | |
| WO | WO-2019148094 A1 * | 8/2019 | ......... | A61B 18/0218 |
| WO | 2020/024612 A1 | 2/2020 | | |
| WO | 2020/232384 A1 | 11/2020 | | |
| WO | 2020/242491 A1 | 12/2020 | | |
| WO | 2021/091566 A1 | 5/2021 | | |
| WO | 2021/190547 A1 | 9/2021 | | |
| WO | 2022/113054 A1 | 6/2022 | | |
| WO | 2022/135375 A1 | 6/2022 | | |

(56) References Cited

FOREIGN PATENT DOCUMENTS

| WO | 2022/166973 A1 | 8/2022 |
| WO | 2022/246158 A1 | 11/2022 |
| WO | 2023/088572 A1 | 5/2023 |

OTHER PUBLICATIONS

Patent Cooperative Treaty, International Search Report, mailed Jul. 25, 2024, in PCT/US2024/023345.

Patent Cooperative Treaty, International Search Report, mailed Jun. 24, 2024, in PCT/US2024/018244.

Patent Cooperative Treaty, Written Opinion, mailed Jul. 17, 2024, in PCT/US2024/022547.

Patent Cooperative Treaty, Written Opinion, mailed Jul. 25, 2024, in PCT/US2024/023345.

Patent Cooperative Treaty, Written Opinion, mailed Jun. 24, 2024, in PCT/US2024/018244.

United States Patent and Trademark Office, Office Action mailed Jul. 12, 2024, for U.S. Appl. No. 18/593,832.

Babaliaros et al., "Emerging Applications for Transseptal Left Heart Catheterization: Old Techniques for New Procedures," J. Am. Coll. Cardiol., 2008; 51:2116-22.

Edwards Lifesciences, "The ALT-FLOW II trial for heart failure," 10 pages (undated).

Tanaka et al., "Treatment of Hepatic Encephalopathy Due to Inferior Mesenteric Vein/Inferior Vena Cava and Gonadal Vein Shunt Using Dual Balloon-Occluded Retrograde Transvenous Obliteration," Cardiovasc Intervent Radiol, 2009, 32:390-393 (published online Oct. 7, 2008).

United States Patent and Trademark Office, Office Action mailed Jun. 20, 2024, for U.S. Appl. No. 18/623,954.

United States Patent and Trademark Office, Office Action mailed May 17, 2024, for U.S. Appl. No. 18/624,014.

Wilson et al., "Successful Tanscatheter Occlusion of an Anomalous Pulmonary Vein With Dual Drainage to the Left Atrium," Catheter Cardiovasc Interv, 2015, 85:1212-1216 (published online in Wiley Online Library, Apr. 7, 2015).

* cited by examiner

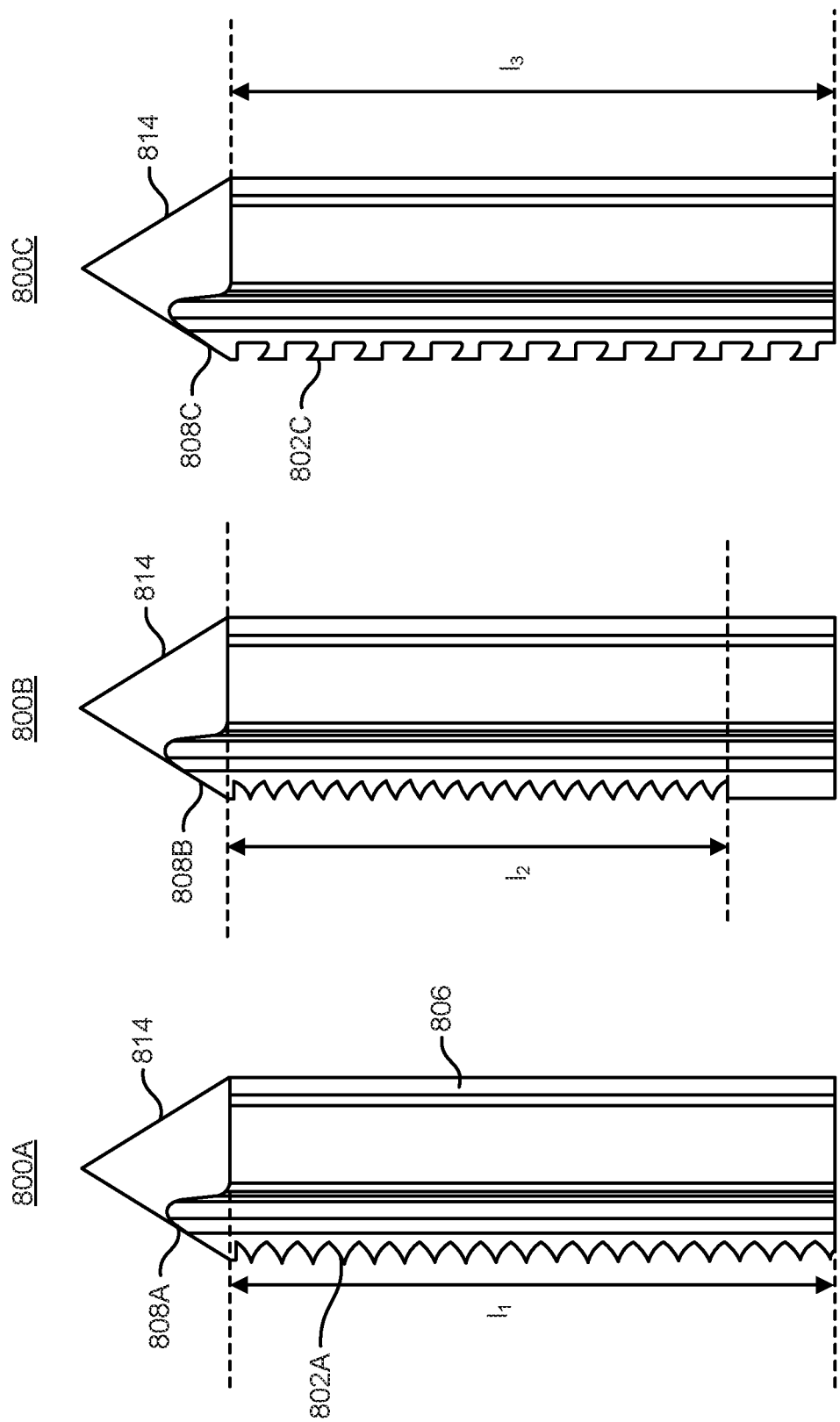

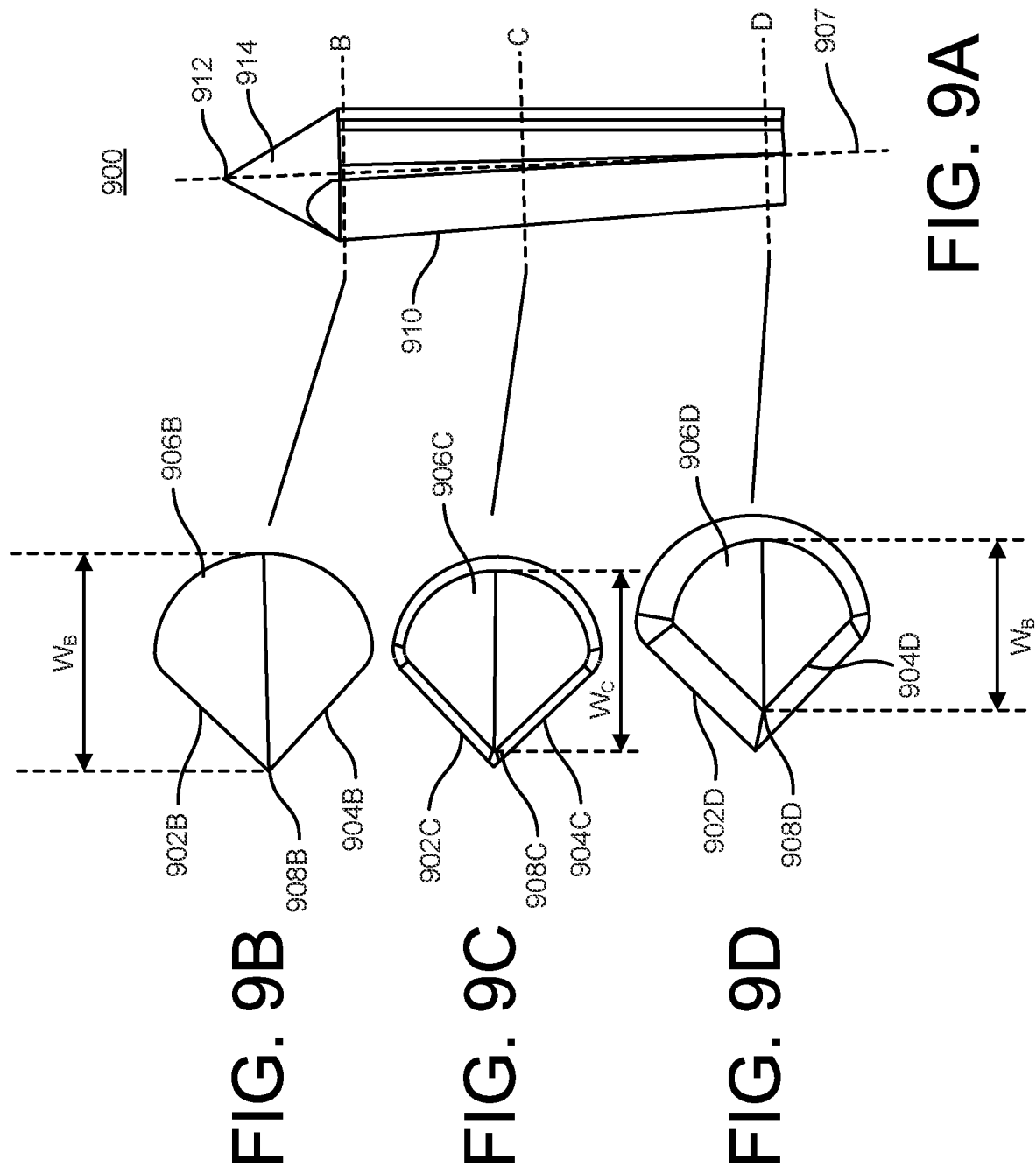

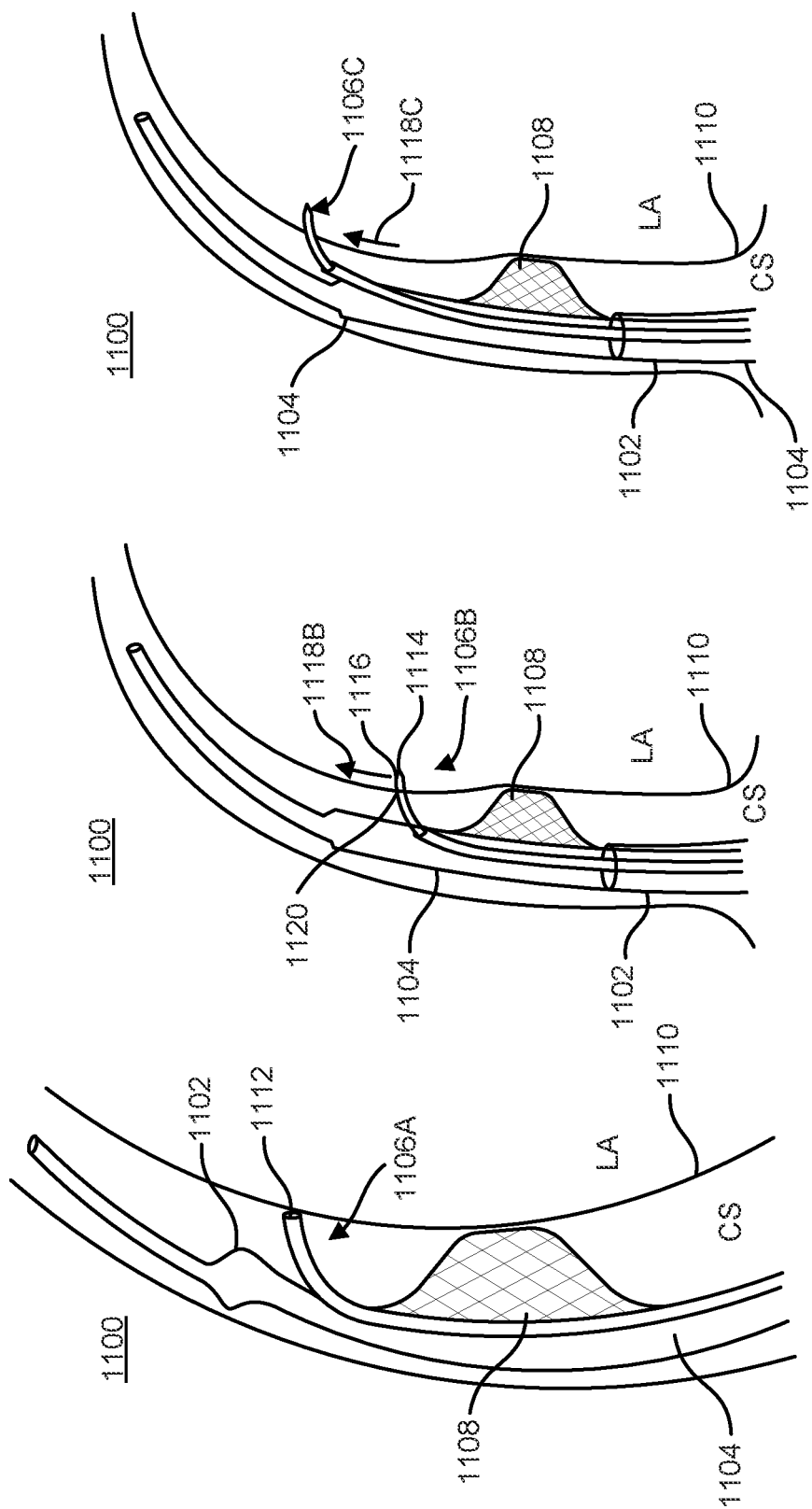

SLICING ELEMENTS FOR SHUNTING CATHETERS

CROSS-REFERENCE TO RELATED APPLICATION

The present application claims the benefit of U.S. Provisional Application No. 63/457,663, entitled "SLICING ELEMENTS FOR SHUNTING CATHETERS," filed on Apr. 6, 2023, which is incorporated by reference herein for all purposes in its entirety.

TECHNICAL FIELD

Certain embodiments of the present disclosure relate to medical systems, apparatus, and methods for creating a shunt in a patient. More specifically, some embodiments of the present disclosure relate to medical systems, apparatus, and methods for creating a shunt on a cardiovascular system wall in a patient.

BACKGROUND

Heart failure is a serious condition that happens when a heart cannot pump enough blood and oxygen to support other organs in your body. Heart failure is classified according to left ventricular (LV) function as "heart failure with reduced ejection fraction (EF)" (HFrEF; EF<40%), "mid-range EF" (HFmrEF; EF 40-49%), or "preserved EF" (HFpEF; EF≥50%). About half the patients with heart failure have HFpEF. HFpEF generally happens when LV and left atrial filling pressures increase significantly during exercise, with an associated increase in pulmonary pressures leading to pulmonary congestion. Structural interventions to lower elevated either left or right atrial filling pressures are gaining attention.

Studies in heart failure show that lowering left atrial pressure may reduce cardiovascular events while improving functional capacity. The creation of an interatrial shunt has emerged as a therapy to decompress the left atrium in patients with acute and chronic left HF. As such, attention has turned toward the development of interatrial shunt devices (IASDs) as a means of reducing the detrimental increase in left-sided filling pressures with exercise in an effort to improve symptomatology. The IASDs may be used to treat various kinds of heart failure and/or other diseases that may result in too high of a pressure in the right atrium of a patient.

SUMMARY

Many IASDs reside in the interatrial septum, with risk for right-to-left shunting and systemic embolization. Moreover, preservation of the interatrial septum is important with an increasing number of left-sided transseptal transcatheter interventions. Ways to improve IASDs for safer and better procedures are needed.

According to some embodiments of the present disclosure, a shunting catheter includes: a catheter shaft including a shaft lumen; and a slicing element including a distal end and a proximal end, and including a slicing element shaft, a puncture element, and a slicer; the slicing element is disposed in the shaft lumen at a first state; the slicing element is extended from the catheter shaft at the proximal end of the slicing element at a second state; and the puncture element is disposed at the distal end of the slicing element.

According to some embodiments, a method for creating a shunt includes: deploying a shunting catheter in a first state, the shunting catheter including: a catheter shaft including a shaft lumen; a slicing element disposed in the shaft lumen at the first state, the slicing element including a slicing element shaft, a puncture element, and a slicer; disposing the shunting catheter approximate to a target location of a patient; operating the shunting catheter to a second state, and the slicing element extends from the catheter shaft at an angle greater than zero degree at the proximal end of the slicing element at the second state; puncturing, using the puncture element, an opening at the target location; and expanding the opening using the slicing element.

According to some embodiments, a shunting catheter system includes: a shunting catheter including: a catheter shaft including a shaft lumen; and a slicing element disposed in the shaft lumen at a first state, the slicing element including a slicing element shaft, a puncture element, and a slicer; an energy source connected to the shunting catheter; and a controller connected to the energy source including one or more processors; the one or more processors are configured to control the energy source to deliver energy to the shunting catheter; and the slicing element is extended from the catheter shaft at the proximal end of the slicing element at a second state.

According to some embodiments, a method for creating a shunt includes: deploying a shunting catheter in a first state, the shunting catheter including: a catheter shaft including a shaft lumen; a slicing element disposed in the shaft lumen at the first state, the slicing element including a slicing element shaft, a puncture element, and a slicer; disposing the shunting catheter approximate to a target location of a patient; operating the shunting catheter to a second state, wherein the slicing element extends from the catheter shaft at the second state; and delivering energy from an energy source to the shunting catheter.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 8A-8C are schematic diagrams of side view of an example of a slicing element, in accordance with embodiments of the present disclosure.

FIGS. 9A-9D are schematic diagrams of a side view and cross-sectional views of an example of a slicing element, in accordance with embodiments of the present disclosure.

FIGS. 11A-11C are schematic diagrams of side views of an example of a shunting catheter, according to certain embodiments of the present disclosure.

Figure 1:
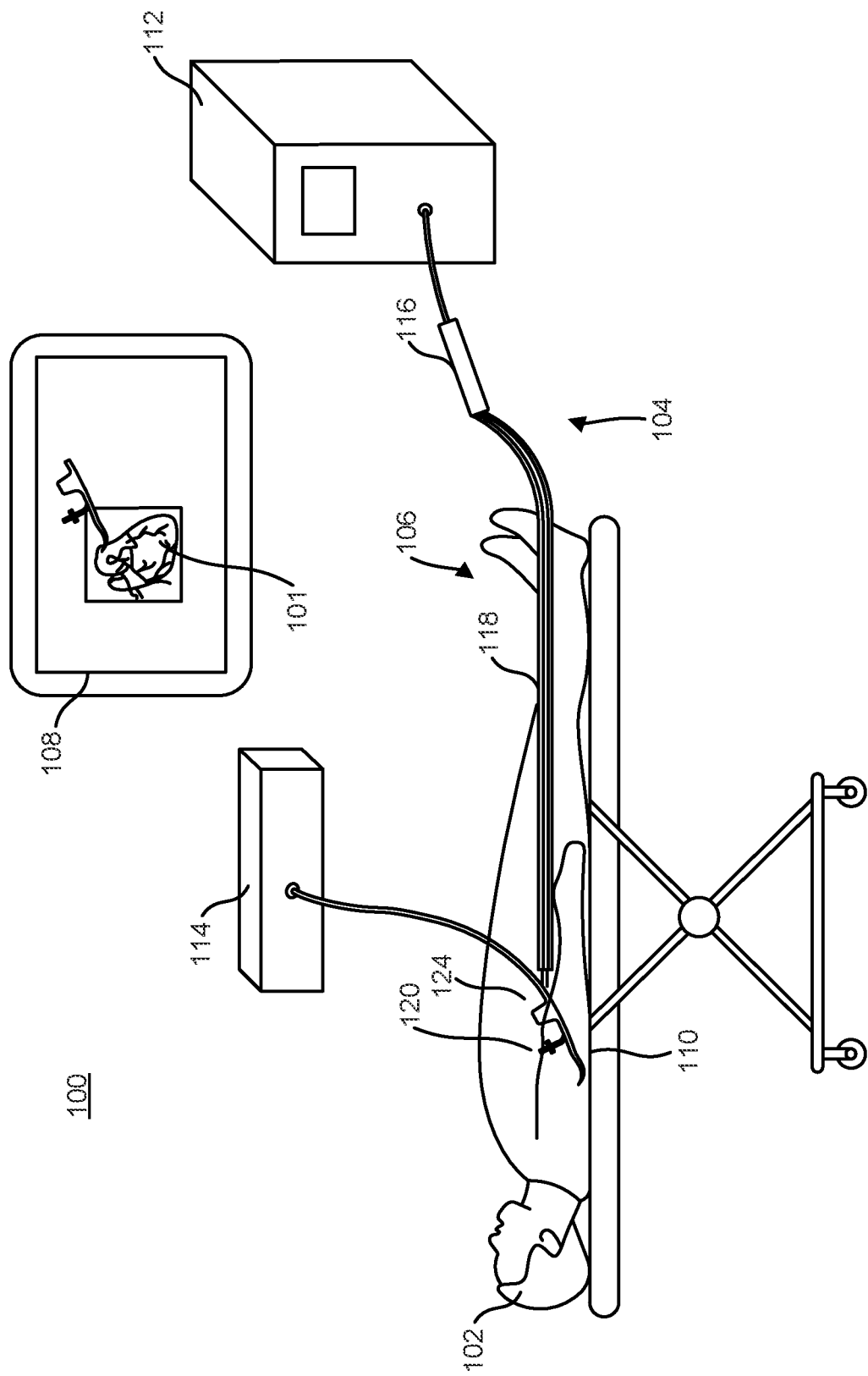
FIG. 1 is a diagram illustrating an exemplary clinical setting for treating a heart of the patient, using a shunting catheter system, in accordance with embodiments of the present disclosure.

While the present disclosure is amenable to various modifications and alternative forms, specific embodiments have been shown by way of example in the drawings and are described in detail below. The present disclosure, however, is not to limit the present disclosure to the particular embodiments described. On the contrary, the present disclosure is intended to cover all modifications, equivalents, and alternatives falling within the scope of the present disclosure as defined by the appended claims.

DETAILED DESCRIPTION

The following detailed description is exemplary in nature and is not intended to limit the scope, applicability, or configuration of the present disclosure in any way. Rather, the following description provides some practical illustrations for implementing exemplary embodiments of the present disclosure. Examples of constructions, materials, and/or dimensions are provided for selected elements. Those skilled in the art will recognize that many of the noted examples have a variety of suitable alternatives.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g., 1 to 5 includes 1, 1.5, 2, 2.75, 3, 3.80, 4, and 5) and any number within that range.

Although illustrative methods may be represented by one or more drawings (e.g., flow diagrams, communication flows, etc.), the drawings should not be interpreted as implying any requirement of, or particular order among or between, various steps disclosed herein. However, some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information. In some embodiments, the term "receive" or "receiving" means obtaining from a data repository (e.g., database), from another system or service, from another software, or from another software component in a same software. In certain embodiments, the term "access" or "accessing" means retrieving data or information, and/or generating data or information.

There are various approaches for creating an interatrial shunt, which is a connection or gateway between the left and right atria of a patient's heart for blood to flow through. In some embodiments, examples of interatrial shunt devices (IASDs) include implants or shunting catheters. For example, devices reside in the interatrial septum, with risk for right-to-left shunting and systemic embolization. In some examples, preservation of the interatrial septum is important with an increasing number of left-sided transseptal transcatheter interventions. Ways to improve IASDs for safer and better procedures are needed. At least some embodiments of the present disclosure are directed to a shunting catheter for deployment through a patient's coronary sinus (CS) for creating a shunt between the CS and the patient's left atrium (LA).

A patient's CS ostium may have a diameter of from about 10 mm to about 20 mm. As the CS is a relatively small vessel, at least some embodiments of the present disclosure include features of a shunting catheter that helps protect a patient's vessels during deployment and/or elements for stabilizing the catheter during the procedure. In embodiments, the shunting catheter includes a catheter shaft including a shaft lumen and a slicing element including a distal end and a proximal end, and comprising a slicing element shaft, a puncture element, and a slicer. In some embodiments, the catheter shaft is made of flexible materials that bends according to the anatomy of the CS to conform to the shape of the patient's CS. In some embodiments, the catheter shaft includes a stabilizing element such as distal tip that has a curve (e.g., a pre-existing curve) conforming to the shape of a patient's CS to help stabilize the catheter and minimize potential damage to the vessel wall of a patient's CS.

In certain embodiments, the slicing element is disposed in the shaft lumen at a first state, and is extended from the catheter shaft at the proximal end of the slicing element at a second state. In some embodiments, the puncture element is disposed at the distal end of the slicing element. In some embodiments, a shunt is formed by creating an opening between the patient's CS and LA. In certain embodiments, the shunting catheter is inserted through the patient's superior vena cava (SVC) via a transjugular approach. In certain embodiments, the shunting catheter is inserted through the patient's inferior vena cava (IVC) via a transfemoral approach.

FIG. 1 is a diagram illustrating an exemplary clinical setting 100 for treating a heart 101 of the patient 102, using a shunting catheter system 104, in accordance with embodiments of the present disclosure. The shunting catheter system 104 includes a shunting device 106. As will be appreciated by the skilled artisan, the clinical setting 100 may have other components and arrangements of components that are not shown in FIG. 1. In some embodiments, the shunting catheter system 104 includes or is coupled to an imaging system (e.g., an X-ray system) which may include one or more visualization elements and a display 108. In some embodiments, one or more visualization elements may be disposed on the shunting device 106. In certain embodiments, the imaging system can help guide a physician's operation of the shunting catheter 110 during procedure.

According to certain embodiments, the shunting device 106 includes a shunting catheter 110, a controller 112, and an energy source 114 (e.g., a generator). The controller 112 is configured to control functional aspects of the shunting device 106. In embodiments, the controller 112 is configured to control the energy source 114 to deliver energy to the shunting catheter 110. The controller 112 may be connected to the one or more visualization elements to facilitate positioning of the shunting catheter 110 in a patient's heart during procedure. In some embodiments, the energy source 114 is connected to the controller 112. In some embodiments, the energy source 114 may be integrated with the controller 112.

According to some embodiments, the shunting device 106 includes a handle 116, a catheter shaft 118, and a slicing element 120 configured to provide shunting at a target location. In certain embodiments, the slicing element 120 includes a puncture element (e.g., a puncture needle) configured to puncture through a vessel wall. In certain embodiments, the slicing element 120 is connected to the energy source 114 to provide shunting. For example, the slicing element 120 may include a slicer configured to receive energy from the energy source 114 to deliver energy (e.g., ablative energy, radiofrequency (RF) energy, thermal energy, pulse ablative energy, microwave, laser, etc.) to the target location (e.g., a target tissue) at a cardiovascular system (e.g., a circulatory system) wall.

In certain embodiments, the handle 116 is configured to be operated by a user to position the slicing element 120 at the desired anatomical location. In some embodiments, the slicing element 120 includes a slicing element shaft, a puncture element, and a slicer. In embodiments, the slicing element shaft having a pre-determined curve. The catheter shaft 118 includes a shaft lumen, and generally defines a longitudinal axis of the shunting catheter 110. In certain embodiments, the slicing element 120 is disposed in the shaft lumen at a first state (e.g., before a deployment and/or during a deployment to position the slicing element 120), and is extended from the catheter shaft 118 at the proximal end of the slicing element at a second state (e.g., a shunting state to use the slicing element).

According to certain embodiments, during deployment, the shunting device 106 including a portion of the catheter shaft 118 enters through a patient's CS ostium. The shunting device 106 may then be oriented through one or more mechanisms in the patient's CS, as will be discussed in more details below. In some embodiments, in order to conform to the shape of the patient's CS, the catheter shaft 118 is made of flexible materials and/or has a structure that may bend according to the anatomy of the CS. In certain embodiments, during deployment, the puncture element creates an opening at a target tissue (e.g., a vessel wall), then the slicer enlarges the opening at the target tissue.

According to some embodiments, the energy source 114 coupled to the shunting catheter 302 may provide various types of energy such as, for example, radiofrequency (RF) energy, phased RF energy, ablative energy, cryogenic ablative energy, thermal energy, pulse energy, laser energy, microwave energy, and/or the like. In certain embodiments, the controller 112 controls the delivery of shunting energy after and/or when the opening is generated by the puncture element and/or the slicing element.

In certain embodiments, the shunting catheter 110 includes an apposition element 124 disposed proximate to the slicing element 120. In some embodiments, the apposition element 124 is disposed within a shaft (e.g., an outer shaft) at the first state. In some embodiments, the apposition element 124 is protruded from the catheter shaft 118 at the first state and/or at the second state. In certain embodiments, the apposition element 124 can appose to a cardiovascular system wall (e.g., the front wall or back wall of the CS, a left atrium wall, a right atrium wall, etc.) at the second state, for example, to help position and/or stabilize the slicing element 120. In certain embodiments, the apposition element 124 includes a braid structure. In some embodiment, the apposition element 124 may include a nitinol braid that can be held within the catheter shaft 118. After deployment and stabilization of the catheter shaft 118, the slicing element 120 including a slicer and a puncture needle may then be deployed. In some embodiments, the slicing element 120 is configured to deliver energy to target tissues for creating a shunt in the patient's CS.

According to some embodiments, various components (e.g., the controller 112) of the shunting catheter system 104 may be implemented on one or more computing devices. A computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the shunting catheter system 104.

In some embodiments, a computing device (e.g., the controller 112) includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices. In some embodiments, various components or parts of components (e.g., controller 112, shunting catheter 110, etc.) can be integrated into a physical device.

In some embodiments, the shunting catheter system 104 includes one or more memories (not illustrated). The one or more memories includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the one or more memories store computer-executable instructions for causing a processor (e.g., the controller 112) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, the memory may include a data repository that may be implemented using any one of the configurations described below. A data repository may include random access memories, flat files, XML files, and/or one or more database management systems (DBMS) executing on one or more database servers or a data center. A database management system may be a relational DBMS (RDBMS), hierarchical DBMS (HDBMS), multidimensional DBMS (MDBMS), object oriented DBMS (ODBMS or OODBMS) or object relational DBMS (ORDBMS), and/or the like. The data repository may be, for example, a single relational database. In some cases, the data repository may include a plurality of databases that can exchange and aggregate data by a data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the shunting catheter system 104 can communicate via or be coupled to via a communication interface, for example, a wired or wireless interface. The communication interface includes, but is not limited to, any wired or wireless short-range and long-range communication interfaces. The wired interface can use cables, umbilicals, and the like. The short-range communication interfaces may be, for example, local area network (LAN), interfaces conforming to known communications standards, such as Bluetooth™ standard, IEEE 802 standards (e.g., IEEE 802.11), a ZigBee™ or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

Figure 2:
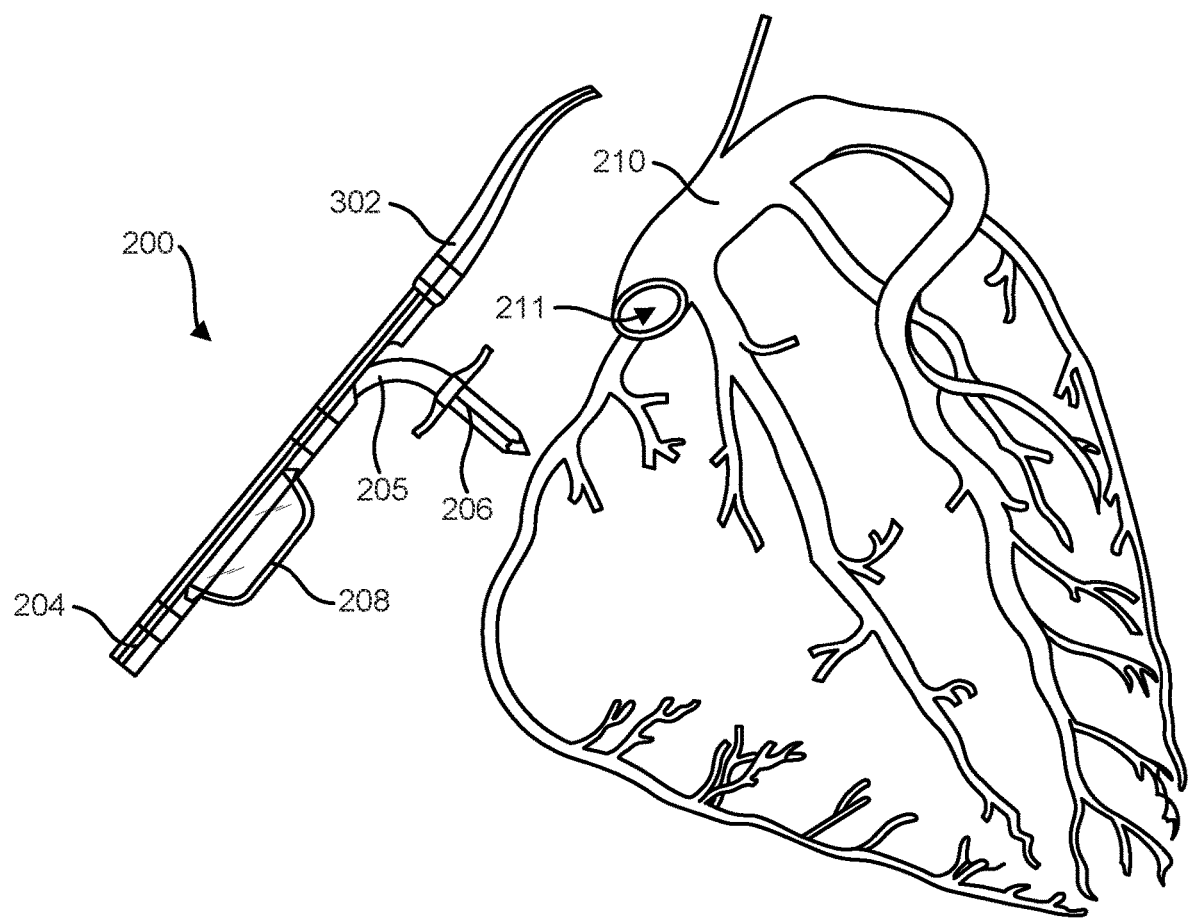
FIG. 2 is a schematic diagram illustrating an example of a shunting device to be deployed in a heart of a patient, in accordance with embodiments of the present disclosure.

FIG. 2 is a schematic diagram illustrating an example of a shunting device 200 to be deployed in a heart of a patient, in accordance with embodiments of the present disclosure. FIG. 2 is merely an example. One of the ordinary skilled in the art would recognize many variations, alternatives, and modifications. As shown, the shunting device 200 includes a shunting catheter 202 to be deployed to a patient's coronary sinus (CS) 210 via the CS ostium 211. In some embodiments, the shunting catheter 202 includes a catheter shaft 204, a slicing element 206, and an apposition element 208. In certain embodiments, the catheter shaft 204 has a curve at its distal end 205. In some embodiments, as illustrated, the slicing element 206 is extended from the catheter shaft 204 at a state to provide shunting (e.g., a second state different from a first state to deploy the catheter 202). In certain examples, the slicing element 206 forms an angle greater than 10 degrees from the distal end 202 of the catheter shaft 204. In some examples, the slicing element 206 forms an angle greater than 30 degrees from the distal end 202 of the catheter shaft 204. In some embodiments, the slicing element 206 forms an angle proximate to 90 degrees from the catheter shaft 204. In some embodiments, the slicing element 206 forms an angle in the range of 10 degrees to 120 degrees from the catheter shaft 204.

In some embodiments, the catheter shaft 204 is made of flexible material that may curve with the anatomy of the patient's CS 210. In certain embodiments, for example, the catheter shaft 204 may include polyether block amide, nylon, silicone, or a combination thereof. In some instances, the catheter shaft 204 may be a multi-layered and multi-material component. In some examples, the catheter shaft 204 is reinforced with a braid and/or can have an etched or casted liner. The braid for reinforcing the catheter shaft 204 may be made of nitinol. The liner may be made from polyetheretherketone (PEEK), polytetrafluoroethylene (PTFE), copolymers of polyamide and polyether, or a combination thereof. In some embodiments, the catheter shaft 204 is coated for lubricity with a hydrophilic coating, or other types of coating suitable for coating a catheter shaft as known by a skilled person in the art.

In some embodiments, the shunting catheter 202 has a diameter of from about 2 mm to about 5 mm. In certain embodiments, the shunting catheter 202 has a diameter from about 2.5 mm to about 4.5 mm. In some embodiments, the shunting catheter has a diameter from about 3 mm to about 4 mm. In certain embodiments, the shunting catheter 202 may have a diameter allowing it to pass through vessels and parts of the cardiovascular system to reach a target location.

Figure 3:
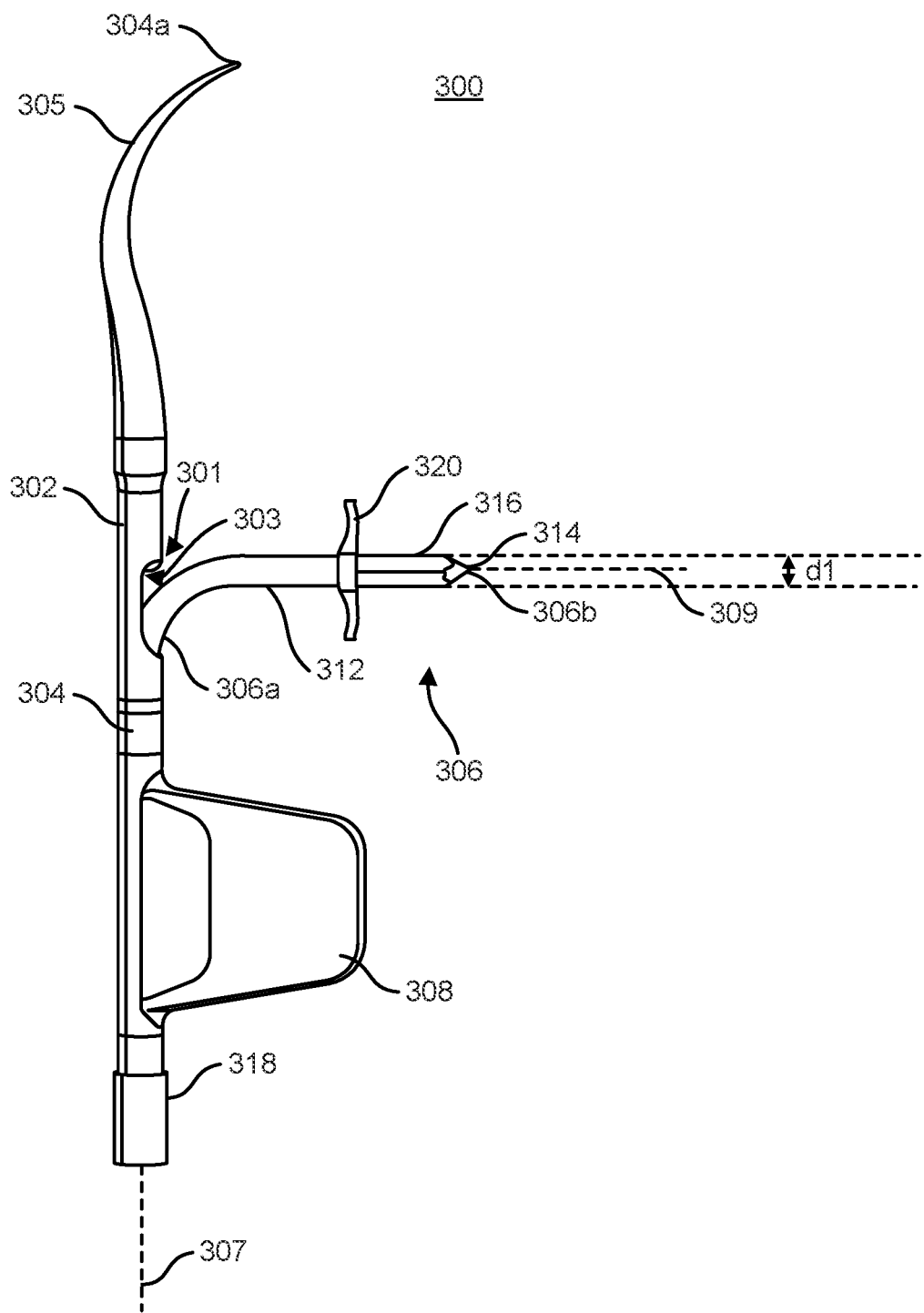
FIG. 3 is a schematic diagram of a side view of an example of a shunting device, in accordance with embodiments of the present disclosure.

FIG. 3 is a schematic diagram of a side view of an example of a shunting device 300, in accordance with embodiments of the present disclosure. FIG. 3 is merely an example. One of the ordinary skilled in the art would recognize many variations, alternatives, and modifications. As shown, the shunting device 300 includes a shunting catheter 302. In some embodiments, the shunting catheter is configured to be delivered through a patient's coronary sinus (CS). In some embodiments, the shunting catheter 302 includes a catheter shaft 304, a slicing element 306, and an apposition element 308.

According to some embodiments, the shunting catheter 302 may be inserted through a small vein in the patient's body, and then tracked to the patient's Right Atrium (RA). Once the shunting catheter 302 is in the patient's RA, the shunting catheter 302 may be maneuvered into the CS ostium to gain alignment in the CS at a target location of on a wall between the patient's CS and LA.

According to certain embodiments, the catheter shaft 304 is made of flexible material that may curve with the anatomy of the patient's CS. In certain embodiments, the catheter shaft 304 may include polyether block amide, nylon, silicone, and/or a combination thereof. In some instances, the catheter shaft 304 may be a multi-layered and multi-material component. In some instances, the shunting catheter 302 may be made from multiple materials that are reflow soldered together. In certain instances, the shunting catheter 302 may be made from multiple materials that are bonded together with an over mold. In certain embodiments, there may be a portion of the shunting catheter 302 that houses other components of the shunting device 300 that are configured to interact with the patient's anatomy.

In some embodiments, the catheter shaft 304 is reinforced with a braid and can have an etched or casted liner. The braid for reinforcing the catheter shaft 304 may be made of nitinol. The liner may be made from polyetheretherketone (PEEK), polytetrafluoroethylene (PTFE), copolymers of polyamide and polyether, or a combination thereof. In certain embodiments, the catheter shaft 304 may be injection molded or extruded. In some embodiments, the catheter shaft 304 is coated for lubricity with a hydrophilic coating, or other types of coating suitable for coating a catheter shaft as known by a skilled person in the art.

In certain embodiments, the catheter shaft 304 may have multiple lumens. In embodiments, the multiple lumens may allow for the exchange and movement of various parts (e.g., the slicing element 306, the apposition element 308) during deployment and/or shunting. In certain embodiments, the shunting catheter 302 is used to gain access into a patient's CS, the shunting catheter 302 including multiple lumens to gain access into the patient's LA.

According to some embodiments, the catheter shaft 304 has a distal end 304a and a proximal end (not shown). In some embodiments, the catheter shaft 304 may include a stabilizing element such as distal tip 305 at the distal end 304a that has a curve (e.g., a pre-existing curve), for example, a curve conforming to the anatomy of a patient's CS. In embodiments, the distal tip 305 may help with navigation when inserting the shunting catheter 302 into the patient's CS. In certain embodiments, the distal tip 305 may allow for proper positioning of the shunting catheter 302 during shunting. In some instances, the distal tip 305 may be made of a different material than other parts of the catheter shaft 304. In some instances, for example, the distal tip 305 may be made of a material more flexible than the material of other parts of the catheter shaft 304. The distal tip 305 may be injection molded or machined to have a unique geometry (e.g., a curve) for better stabilizing the catheter shaft 304 during deployment.

According to some embodiments, the distal tip 305 may have a length of from about 5 mm to about 85 mm. In certain embodiments, the catheter shaft 304 includes a shaft opening 303. In some embodiments, a portion of the catheter shaft 304 between the shaft opening 303 and the distal end 304a has a curve. In some embodiments, the catheter shaft 304 defines a first axis 307, and the slicing element 306 defines a second axis 309 at the second state after deployment. In certain embodiments, the second axis 309 and the first axis 307 form an angle greater than zero degree. In certain embodiments, the second axis 309 and the first axis 307 form an angle greater than 10 degrees.

According to certain embodiments, the catheter shaft 304 includes a shaft lumen 301, and the slicing element 306 is disposed in the shaft lumen 301 at a first state (e.g., during deployment, during deployment to position of the slicing element 306). The slicing element 306 includes a distal end 306a and a proximal end 306b. In some embodiments, the slicing element 306 includes a slicing element shaft 312, a puncture element 314, and a slicer 316. In certain embodiments, the slicing element shaft 312 has a pre-determined curve. In some examples, the slicing element shaft 312 has a pre-determined curve for the slicing element 306 to deploy. In certain embodiments, the slicing element 306 is extended from the catheter shaft 304 at the proximal end 306b of the slicing element 306 at a second state (e.g., a shunting state to use the slicing element). In some instances, the slicing element 306 extends from the catheter shaft 304 through the shaft opening 303. In certain instances, the slicing element 306, including the puncture element 314 and the slicer 316, has a diameter (d1) in the range of about 2 millimeters to about 5 millimeters.

Once the shunting catheter 302 is in position after deployment, the slicing element 306 may be used to puncture through the wall between a patient's CS and LA with the puncture element 314. In some embodiments, the shunting catheter 302 including the slicer 316 may be translated forward, rotated, and/or bended to create a slicing mechanism. In some embodiments, the shunting catheter 302 may utilize energy to create an easier slicing mechanism as well as solidify the shunt geometry post-slicing.

According to certain embodiments, an energy source coupled to the shunting catheter 302 may provide various types of energy such as, for example, radiofrequency (RF) energy, phased RF energy, ablative energy, cryogenic ablative energy, thermal energy, pulse energy, laser energy, microwave energy, and/or the like. In some embodiments, the energy may be dissipated across a larger portion (e.g., a metallic portion) of the slicing element 306. In some embodiments, the energy may be localized to a point, an edge, or one or more sides of the slicing element 306.

In some embodiments, the slicer 316 may be translated forward to create a slicing mechanism without moving the shunting catheter 302. In certain embodiments, the shunting catheter 302 or the slicer 316 may translate a distance of 0 mm to about 15 mm along a cardiovascular wall (e.g., the wall between a patient's CS and LA). In some embodiments, the slicing element 306 may have ablation integration for ease of slicing through the target tissue. In some instances, before deployment, the slicing element 306 is disposed in the shunting catheter 302 within a shaft lumen (e.g., the shaft lumen 301) where the slicing element 306 can translate through to be deployed.

According to some embodiments, the puncture element 314 is disposed at the distal end 306a of the slicing element 306. In embodiments, the shaft opening 303 is not at the distal end 304a of the catheter shaft 304. In certain embodiments, the puncture element 314 has a configuration of regular trocar point, regular taper point, regular taper cutting, regular reverse cutting edge, regular diamond point, regular conventual cutting edge, regular blunt taper point, premium lancet point, premium diamond point, or premium cutting edge. In certain embodiments, the puncture element 314 is made of materials including nitinol, stainless steel, cobalt chromium, aluminum, and/or a combination thereof.

According to certain embodiments, the slicer 316 has a cross-sectional shape generally perpendicular to the second axis 309. In some embodiments, the slicer 316 has a circular cross-sectional shape generally perpendicular to the second axis 309. In some embodiments, the slicer 316 has a non-circular cross-sectional shape generally perpendicular to the second axis 309. In some embodiments, the non-circular cross-sectional shape of a slicer 316 may have a sharp edge to allow for ease of slicing through the target tissue.

In embodiments, the slicer 316 is configured to deliver energy to a target tissue during shunting. The energy delivered by the slicing element may include ablative energy, radiofrequency (RF) energy, phased RF energy, thermal energy, pulse energy, microwave energy, laser energy, or ultrasonic energy. In certain embodiments, the energy delivered by the slicing element slices through tissue surrounding the target location to create an opening at the target location. In some embodiments, the energy delivered by the slicing element ablates tissue surrounding the target location to solidify an opening at the target location. In certain embodiments, delivering energy through the slicer 316 helps slice through target tissue during shunting. In certain embodiments, delivering energy through the slicer 316 helps prevent tissue regrowth around the created shunt after the procedure.

According to some embodiments, the shunting catheter 302 further includes an outer shaft 318 disposed outside of at least a part of the catheter shaft 304 during deployment. In some embodiments, the outer shaft 318 is made of flexible material that may curve with the anatomy of the patient's CS. In certain embodiments, for example, the outer shaft 318 may include polyether block amide, nylon, silicone, or a combination thereof. In some instances, the outer shaft 318 may be a multi-layered and multi-material component.

In some examples, the outer shaft 318 is reinforced with a braid and can have an etched or casted liner. The braid for reinforcing the catheter shaft 304 may be made of nitinol. The liner may be made from polyetheretherketone (PEEK), polytetrafluoroethylene (PTFE), copolymers of polyamide and polyether, or a combination thereof. In some instances, the outer shaft 318 may include a reinforcing element (e.g., a laser cut tube). In certain embodiments, the outer shaft 318 may be injection molded or extruded. In some embodiments, the catheter shaft 304 is coated for lubricity with a hydrophilic coating, or other types of coating suitable for coating a catheter shaft as known by a skilled person in the art.

In certain examples, the outer shaft 318 and/or the catheter shaft 304 may serve the purpose of housing all of the catheter components until the desired target location is reached. Once the shunting catheter 302 has reached the target location, the outer shaft 318 may translate towards the proximal end of the catheter shaft 304 to expose the slicing element 306 and other components.

According to certain embodiments, the apposition element 308 is disposed within the outer shaft 318 at a first state (e.g., during deployment). In embodiments, the apposition element 308 protrudes from the catheter shaft 304 during deployment. The apposition element 308 is flexible and compressed to fit within the outer shaft 318, and configured to decompress and protrude from the catheter shaft 304 during deployment. In some embodiments, the apposition element 308 is disposed proximate to the slicing element 306 and/or the one or more shaft openings 303. In some instances, the apposition element 308 is a braided structure including one or more nickel titanium wires. In some instances, the apposition element 308 is made of a flexible material having a portion protruding from the catheter shaft 304. In some examples, the flexible material may be a foam. In some instances, the flexible material may be a balloon filled with a contrast solution that shows up under fluoroscopy. In some instances, the flexible material may be a polymer with a radiopaque marker added for visualization. The radiopaque marker may include tantalum, gold, or any radiopaque maker known by a skilled person in the art.

In certain embodiments, the apposition element 308 is configured to appose at least one wall in a patient's cardiovascular system (e.g., CS, LA, etc.) such that the shunting catheter 302 is stabilized in one position once deployed. According to some embodiments, the apposition element 308 has several benefits, one of which is the stabilization of catheter 302 after deployment. Any movement or lack thereof the protruding element (e.g., a braided element) provides an estimated distance of how far the catheter 302 is away from the vessel wall of patient's CS. In addition, in instances where the apposition element 308 includes a braided element, such that when the braided element is apposing the vessel wall of a patient's CS, the openings between the braids still allow blood flow through the apposition element 308, thus reducing the risk of thrombus formation caused by any occlusion in the vessel.

The apposition element 308 may be made of nitinol, and is reflow soldered or bonded to the catheter shaft 304. In some embodiments, the apposition element 308 serves the purpose of pushing against back wall of a patient's CS, to allow for the shunting catheter 302 to translate forward and against target location on a wall between patient's CS and LA. The apposition element 308 may include an elastic braided structure, and may thus expand and compress with force applied by the outer shaft 318, or through other mechanical means.

In some embodiments, for example as shown, the apposition element 308 is disposed on the same side of the catheter shaft 304 as the slicing element 306. In some embodiments, the apposition element 308 may be on an opposite side of the catheter shaft 304 from the slicing element 306. In certain embodiments, the apposition element 308 may be configured to appose the wall between patient's CS and LA, instead of the back of patient's CS wall. This may allow for an inner catheter (e.g., the slicing element shaft 312) or the slicing element 306 to then penetrate through the patient's CS wall to gain access into the patient's LA. In embodiments, the apposition element 308 helps stabilize and position the shunting catheter 302 in the patient's CS at a target location.

According to some embodiments, the slicing element 306 includes a mechanical indicator 320 to notify the user when contact with the wall between patient's CS and LA has been reached. In some instances, the mechanical indicator 320 may be made from a nitinol braid. In certain instances, the mechanical indicator 320 may run parallel to the wall. In certain instances, the mechanical indicator 320 may being orthogonal to the wall In certain embodiments, the mechanical indictor 320 may take on various geometric shapes including, but not limited to, a uniform bowl shape or two tabs that are radiopaque under fluoroscopy. In some embodiments, the mechanical indicator 320 may have high density radiopaque markers either weaved into a braid or is attached onto the mechanical indicator 320. The radiopaque marker may include materials including, for example, gold, tantalum, platinum, nickel-titanium-platinum alloy, bismuth, iodine, barium, and/or a combination thereof.

In some embodiments, the mechanical indicator 320 may also serve as a mechanical stop to ensure the slicing device is not protruding further into the patient's LA than intended. In certain embodiments, the mechanical indicator 320 is made from a variety or combination of many different materials, for example, different medical polymers and metallic alloys. In some instances, the metallic alloys of the mechanical indicator 320 includes nitinol, stainless steel, and/or a combination thereof.

Figure 4:
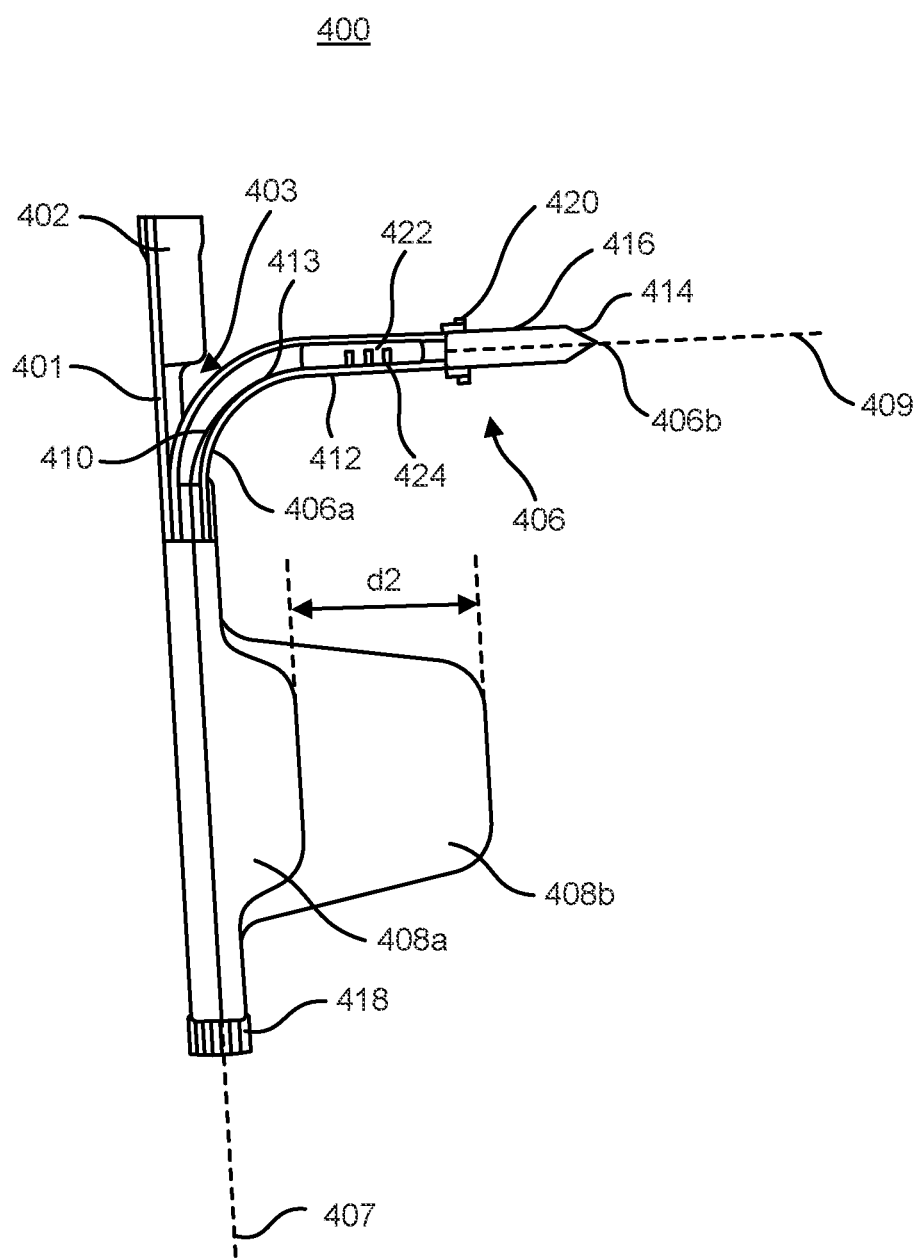
FIG. 4 is a schematic diagram of a cross-sectional view of an example of a shunting catheter, in accordance with embodiments of the present disclosure.

FIG. 4 is a schematic diagram of a cross-sectional view of an example of a shunting catheter 400, in accordance with embodiments of the present disclosure. FIG. 4 is merely an example. One of the ordinary skilled in the art would recognize many variations, alternatives, and modifications. As shown, the shunting catheter 400 includes a catheter shaft 402 having a shaft lumen 401, a shaft opening 403, and a slicing element 406 disposed within the shaft lumen 401 at a first state (e.g., during deployment, during deployment to position of the slicing element 406). In some embodiments, the slicing element 406 is extended from the catheter shaft 402 at a second state (e.g., during shunting/slicing).

According to certain embodiments, the shunting catheter 400 includes an apposition element 408a-b configured to be disposed within the shaft lumen 401 at a first state (e.g., 408a during deployment), and protrudes further from the catheter shaft 402 at a second state (e.g., 408b during shunting/slicing). The difference (d2) between the thickness of the apposition element 408a at a first state and the protrusion height of the apposition element 408b at a second state may be from about 3 mm to about 20 mm. According to some embodiments, for example during the tracking of the shunting catheter 400 to a target location in a patient's CS, the slicing element 406 may be translated out of the catheter lumen 401 to puncture a target location on a wall between a patient's CS and LA.

As shown, the slicing element 406 includes a distal end 406a and a proximal end 406b. In some embodiments, the slicing element 406 includes a slicing element shaft 412, a puncture element 414, and a slicer 416. In certain embodiments, the slicing element shaft 412 has a pre-determined curve. In some examples, the slicing element shaft 412 has a pre-determined curve for the slicing element 406 to deploy. In certain embodiments, the slicing element 406 is extended from the catheter shaft 402 at the proximal end 406b of the slicing element 406 at a second state (e.g., a shunting/slicing state to use the slicing element). In some instances, the slicing element 406 extends from the catheter shaft 402 through the shaft opening 403. In certain instances, the slicing element 406 has a diameter (d1) in the range of about 2 millimeters to about 5 millimeters.

According to certain embodiments, the slicing element shaft 412 may include an internal guidewire or pull wire 410 that allows for maneuverability and control over the trajectory of the puncture element 414. In some instances, the pull wire 410 may be a pull wire assembly. In certain instances, the pull wire 410 is configured to control the flex or angle of the puncture element 414 relative to a wall between a patient's CS and LA.

In some embodiments, the slicing element 406 may have a telescoping feature (e.g., puncture element 414 is retractable into the slicing element shaft 412) to allow for the blunt end of the slicing element shaft 412 to contact the wall between patient's LA and CS before the puncture element 414 is translated forward to make contact with the wall between patient's LA and CS. In embodiments, the telescoping feature of the slicing element 406 allows for a safe delivery of the puncture element 414 to the target location.

According to some embodiments, the catheter shaft 402 defines a first axis 407, and the slicing element 406 defines a second axis 409. In certain embodiments, the second axis 409 and the first axis 407 form an angle greater than zero degree. In certain examples, the second axis 409 and the first axis 407 form an angle greater than 10 degrees. In some embodiments, the second axis 409 and the first axis 407 form an angle proximate to 90 degrees. In some embodiments, the second axis 409 and the first axis 407 form an angle in the range of 30 degrees to 120 degrees. In some instances, the catheter shaft 402 includes a pre-curve formed from a semi-rigid or rigid material connected to the slicing element 406. The semi-rigid or rigid material may include nitinol or stainless steel (SS) with a curve built in before deployment.

In some embodiments, the slicing element shaft 412 includes a curved portion 413 that forms an arc connecting a first straight portion of slicing element shaft disposed inside the shaft lumen 404 and a second straight portion of the slicing element shaft 412 extended outward from the shaft lumen 401. In embodiments, for example as shown, the curved portion 413 of the slicing element shaft 412 is adjacent the shaft opening 403. In certain embodiments, the slicing element 406 is located at the second straight portion of the slicing element shaft 412 towards the distal end 406a of the slicing element 406.

According to certain embodiments, the shunting catheter 400 may further include an outer shaft 418 disposed outside of the catheter shaft 402 and enclosing the catheter shaft 402, the slicing element 406, and the apposition element 408 in a compressed state before shunting. The outer shaft 418 may have a diameter of from about 8 French (8/3 millimeters) to about 18 French (6 millimeters), or from about 8.5 French (8.5/3 millimeters) to about 16 French (16/3 millimeters), or from about 9 to about 14 French (14/3 millimeters), or from about 9.5 (9.5/3 millimeters) to about 12 French (4 millimeters), or may have a diameter encompassed within these ranges. In some embodiments, for example during deployment, the outer shaft 418 is pulled back to deploy and/or position the catheter shaft 402 including the apposition element 408 and the slicing element 406.

In certain embodiments, the shunting catheter 400 includes multiple compartments (e.g., lumens) for various elements to provide more targeted control during deployment. For example, the shunting catheter 400 may include an additional lumen in between the catheter shaft 402 and the slicing element shaft 412 for more precise control during deployment of the slicing element 406. Similarly, for example, the shunting catheter 400 may include an additional lumen in between outer shaft 418 and the catheter shaft 402 for more precise control during deployment of the apposition element 408a-b. In some embodiments, the shunting catheter 400 may include lumens for containing functional components (e.g., the pull wire 410). In some embodiments, the shunting catheter 400 may include additional lumens for holding shunted tissue from a vessel wall.

In some embodiments, the slicing element includes a mechanical indicator 420. In certain embodiments, the mechanical indictor 420 may take on various geometric shapes including, but not limited to, a uniform bowl shape or two tabs that are radiopaque under fluoroscopy. In some embodiments, the mechanical indicator 420 may have high density radiopaque markers either weaved into a braid or is attached onto the mechanical indicator 420. The radiopaque marker may include materials including, for example, gold, tantalum, platinum, nickel-titanium-platinum alloy, bismuth, iodine, barium, and/or a combination thereof. In some embodiments, the mechanical indicator 420 may also serve as a mechanical stop to ensure the slicing device is not protruding further into the patient's LA than intended.

In certain embodiments, the slicing element 406 includes a tube 422 (e.g., a hypotube) to support the slicing element 406. The tube 422 may include a plurality of laser cuts 424 generally perpendicular to an axis 409 defined by the slicing element 406. In some instances, the axis 409 is perpendicular to a wall between patient's CS and LA. In some instances, the axis 409 is at an angle of about 80 to about 100 degrees to a wall between patient's CS and LA.

In some instances, the tube 422 is made of a semi-rigid or rigid material (e.g., stainless steel or nitinol). In certain instances, the tube 422 is made of relatively rigid material disposed along the axis 409 to help support the slicing element 406 when puncturing through a wall with the puncture element 414. The plurality of laser cuts 424 allows the tube 422 to bend in a certain direction while maintaining rigidity of the slicing element 406 along the axis 409. In some embodiments, the slicing element shaft 412 has a preformed curve 413 that includes a radius upon deployment. In certain embodiments, the puncture element 414 is made of materials including nitinol, stainless steel, cobalt chromium, aluminum, and/or a combination thereof.

In some embodiments, the tube 422 is coupled to the pull wire 410. In some embodiments, the tube 422 is made from stainless steel, nitinol, or a metallic alloy. In certain embodiments, the tube 422 is coupled to a pull wire assembly and configured to help with guiding the direction of the curve 413. In some embodiments, the tube 422 is coupled to the pull wire 410 to help ensure that the slicing element 406 does not shift in its trajectory during contact with the vessel wall.

Figures 5A, 5B:
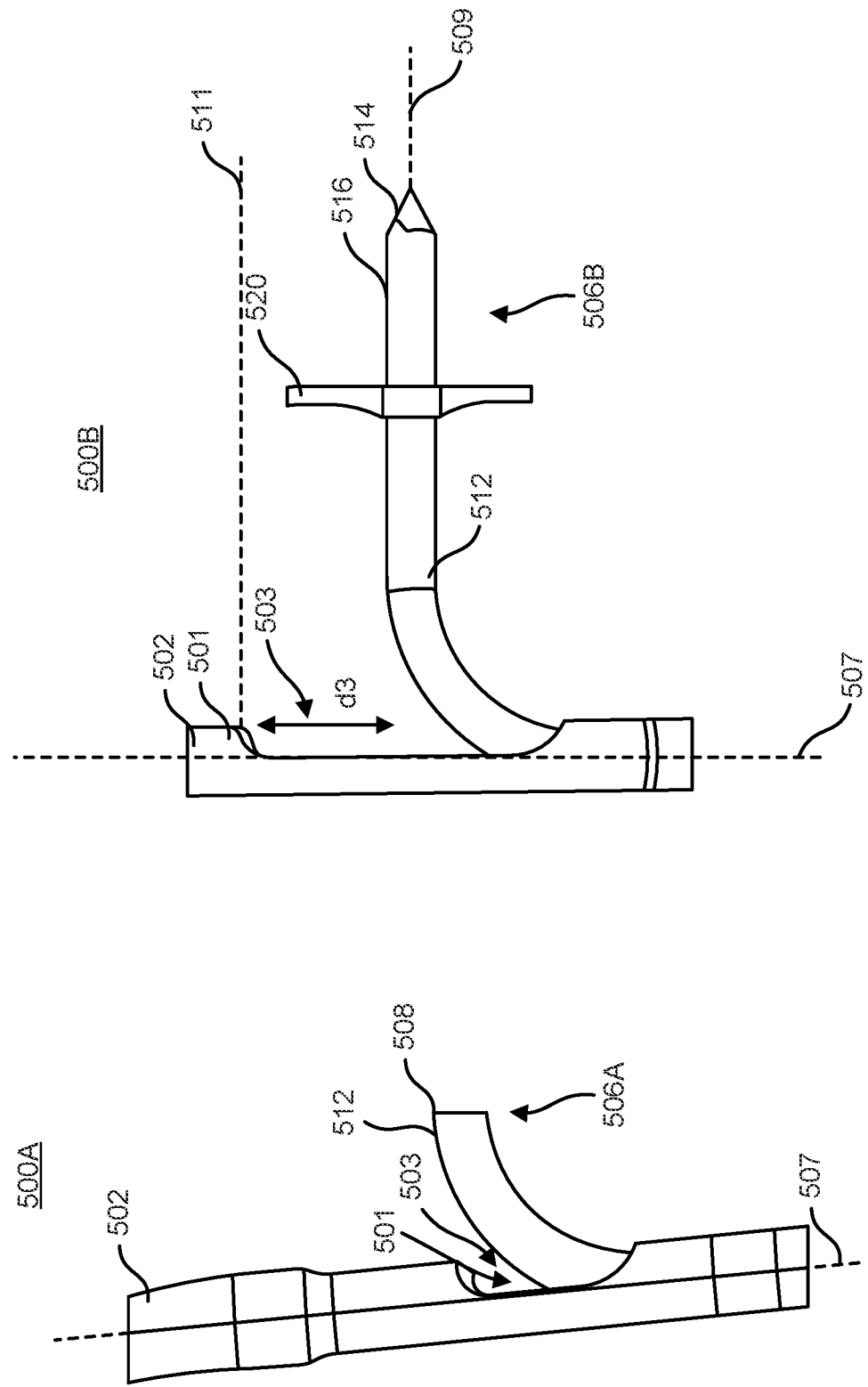
FIGS. 5A-5B are schematic diagrams of side views of an example of a shunting catheter, in accordance with embodiments of the present disclosure.

FIGS. 5A-5B are schematic diagrams of side views of an example of a shunting catheter 500, in accordance with embodiments of the present disclosure. As shown in FIGS. 5A-5B, the shunting catheter 500 includes a catheter shaft 502 having a shaft lumen 501, a shaft opening 503, and a slicing element 506A-506B disposed within the shaft lumen 501 at a first state (e.g., during deployment, during deployment to position of the slicing element 506A-506B), and extended from the catheter shaft 502 at a second state (e.g., during shunting/slicing). In some embodiments, the slicing element 506A-B includes a slicing element shaft 512 having a predetermined curve for the slicing element to deploy, a puncture element 514, a slicer 516, and a mechanical indicator 520.

According to some embodiments, the slicing element 506A and/or 506B may have a telescoping feature (e.g., puncture element 514 is retractable into the slicing element shaft 512) to allow for the blunt end of the slicing element shaft 512 to contact the wall between patient's LA and CS before the puncture element 514 is translated forward to make contact with the wall between patient's LA and CS. In embodiments, the telescoping feature of the slicing element 506A-506B allows for a safe delivery of the puncture element 514 to the target location.

In some embodiments, for example as shown in FIG. 5A, the slicing element 506A has a first deployed state where the slicing element 506A is extended from the shaft opening 503, and the puncture element 514, the slicer 516, and the mechanical indicator 520 are all retracted and crimped inside the slicing element shaft 512. As shown, the distal end 508 of the slicing element 506A is blunt during the first deployment state, such that if adjustment of position is needed, the vessel wall not at the target location would only make contact with a blunt surface of the slicing element 506A.

In some embodiments, for example as shown in FIG. 5B, the slicing element 506B has a second deployed state where the slicing element 506B is extended from the shaft opening 503, and the puncture element 514, the slicer 516, and the mechanical indicator 520 are all protruded from the slicing element shaft 512. In certain embodiments, the puncture element 514 is made of materials including nitinol, stainless steel, cobalt chromium, aluminum, and/or a combination thereof.

According to certain embodiments, the slicing element 506A-B of the shunting catheter 500 has a first deployment state (e.g., shown in FIG. 5A) and a second deployment state (e.g., shown in FIG. 5B). In some embodiments, the puncture element 514 is retracted in a cavity of the slicing element shaft 512 at the first deployed state. In some embodiments, the puncture element 514 is extended from a distal end 508 of the slicing element shaft 512 at the second deployed state.

In certain embodiments, the shaft opening 503 includes an edge defining an opening axis 511. The opening axis 511 may be generally perpendicular to a first axis 507 along the catheter shaft 502. In some embodiments, the distance (d3) between the opening axis 511 and a second axis 509 along the slicing element 506B may be from about 3 mm to about 20 mm.

Figure 6B:
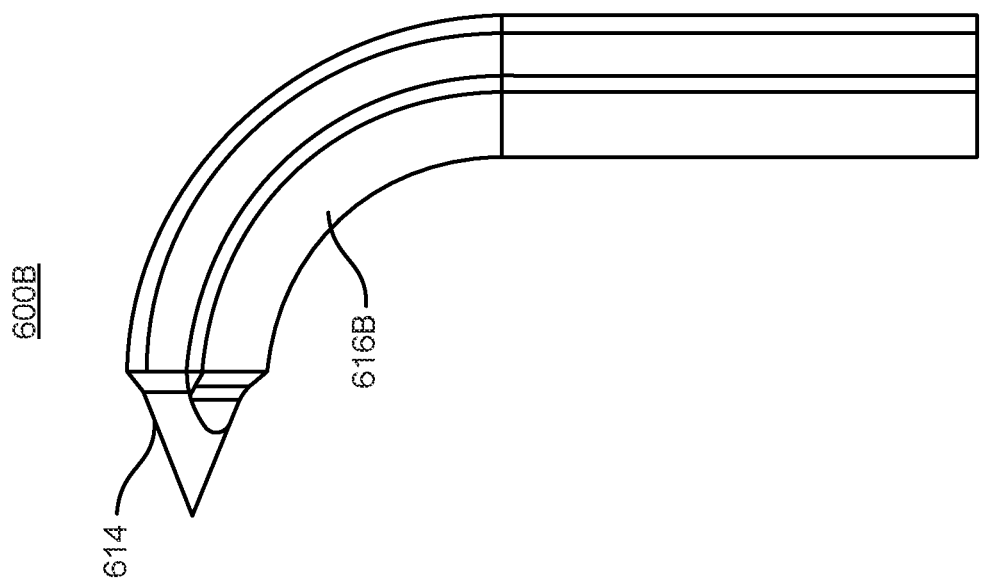
FIGS. 6A-6B are schematic diagrams of side views of an example of a slicing element, in accordance with embodiments of the present disclosure.
Figure 6A:
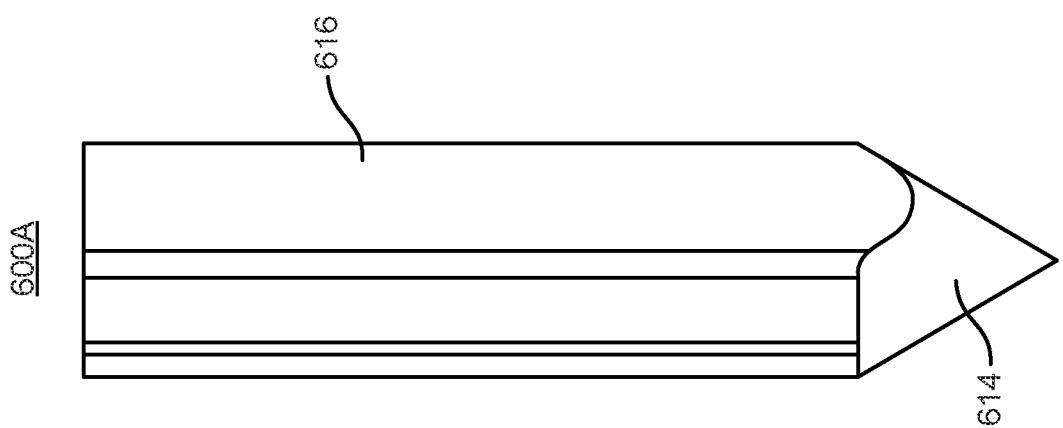

FIGS. 6A-6B are schematic diagrams of side views of an example of a slicing element 600A-B, in accordance with embodiments of the present disclosure. The slicing element 600A-B may include a puncture element 614 and a slicer 616A-B having a sharp edge. The puncture element 614 may be configured such that the slicing element 600A punctures through a vessel wall. In some embodiments, the vessel wall is between the CS and LA of a patient.

According to some embodiments, the puncture element 614 (e.g., a needle) may take on many different needle configurations. Configurations for the puncture element 614 may include, but not limited to, regular trocar point, regular taper point, regular taper cutting, regular reverse cutting edge, regular diamond point, regular conventual cutting edge, regular blunt taper point, premium lancet point, premium diamond point, and/or premium cutting edge. In certain embodiments, the puncture element 614 is made of materials including nitinol, stainless steel, cobalt chromium, aluminum, and/or a combination thereof.

According to some embodiments, the slicing element may take on a plurality of geometries. In some embodiments, for example as shown in FIG. 6A, the slicing element 600A includes a slicer 616A that is straight. In certain embodiments, for example as shown in FIG. 6B, the slicing element 600B includes a slicer 616B having a curved shape. In embodiments, slicer 616B having a curved shape may allow for a hooking type motion as the slicing element 600B slice through a vessel wall to create a shunt. In some embodiments, the slicer 616B is integrated with a slicing element shaft.

In certain embodiments, the slicing element 600A-B may be steerable through the use of pull wires. In some embodiments, the slicing element 600A-B may be steerable through the use of an internal curved shaft. In some instances, the slicing element 600A-600B is made of a super-elastic material (e.g., nitinol). Elastic material allows flexibility in the deployment and retraction of the slicing element 600A-B in and out of a slicing element shaft and/or a catheter shaft, such that the slicing element 600A-B may be easily pulled back into a shaft lumen after shunting.

Figure 7C:
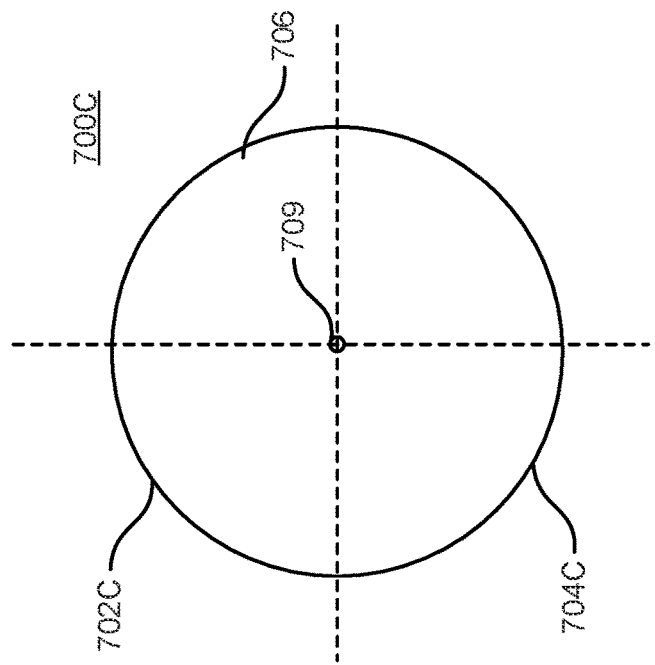
FIGS. 7A-7C are schematic diagrams of cross-sectional views of an example of a slicing element, in accordance with embodiments of the present disclosure.
Figure 7A:
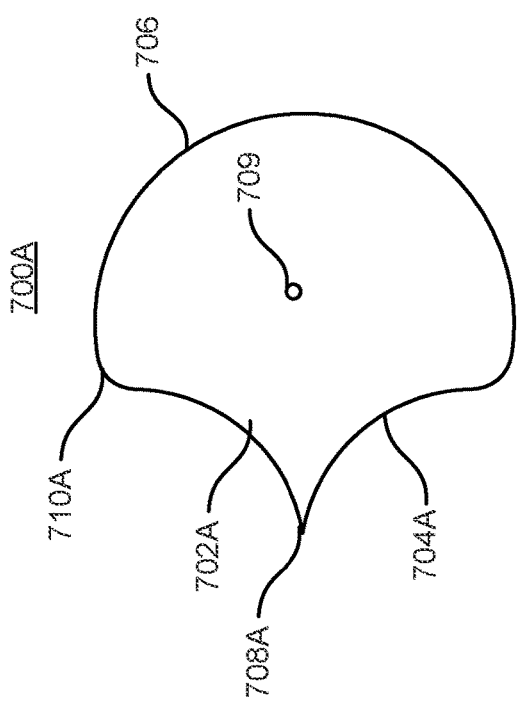
Figure 7B:
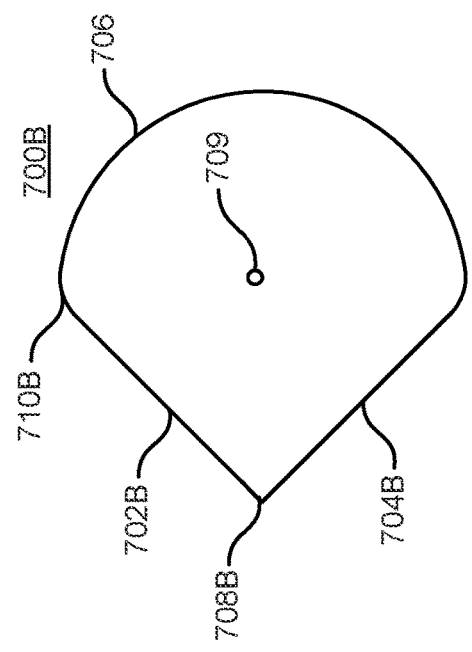

FIGS. 7A-7C are schematic diagrams of cross-sectional views of an example of slicing elements 700A-C, in accordance with embodiments of the present disclosure. According to some embodiments, for example as shown in FIG. 7A, the slicing element 700A has a cross-sectional shape generally perpendicular to a second axis 709 along the length of the slicing element 700A. The cross-sectional shape includes two sides 702A, 704A, and an arc 706. In some embodiments, at least one of the two sides 702A and 704A is a curve. In some embodiments, for example as shown in FIG. 7A, both of the two sides 702A and 704A includes an inward curve (e.g., curvature of the side 702A between a blunt end 710A and a pointy end or point 708A curves towards the second axis 709). In embodiments, both sides 702A and 704A being curved forms a sharper edge along the length of the slicing element 700A on the slicer, such that the slicing element 700A may be more energy efficient during slicing. In certain examples, both sides 702A and 704A being curved may also form a sharper puncture element such that puncturing through a vessel wall is more energy efficient.

According to some embodiments, for example as shown in FIG. 7B, the slicing element 700B has a cross-sectional shape generally perpendicular to a second axis (not shown) defined along the length of the slicing element 700B. The cross-sectional shape includes two sides 702B, 704B, and an arc 706. In certain embodiments, the two sides 702B and 704B of the cross-sectional shape form an angle less than 90 degrees. In certain embodiments, the two sides 702B and 704B of the cross-sectional shape form an angle of from about 20 to about 70 degrees. In certain embodiments, the two sides 702B and 704B of the cross-sectional shape form an angle of about 45 degrees. In some embodiments, one of the two sides (e.g., 708B) includes a straight line connecting a blunt end 710B and a pointy end 708B. In some embodiments, both sides 702B and 704B may be straight.

According to some embodiments, for example as shown in FIG. 7C, the slicing element 700C has a cross-sectional shape generally perpendicular to a second axis 709 along the length of the slicing element 700C. The cross-sectional shape includes two sides 7020, 704C and an arc 706. In some embodiments, at least one of the two sides 702C and 704C is a curve. In some embodiments, for example as shown in FIG. 7C, both of the two sides 702C and 704C include an outward curve (e.g., curvature of the side 702C curves away from the second axis 709). As both sides 702C and 704C curves outward, forming an arc on the side of the slicer, the cross-sectional shape is circular for slicing element 700C.

In embodiments, the slicing elements 700A-C is configured to deliver energy to a target tissue during shunting. The energy delivered by the slicing element 700A-C may include ablative energy, radiofrequency (RF) energy, phased RF energy, thermal energy, pulse energy, microwave energy, laser energy, or ultrasonic energy. In certain embodiments, the energy delivered by the slicing element 700A-C slices through tissue surrounding the target location to create an opening at the target location. In some embodiments, the energy delivered by the slicing element 700A-C ablates tissue surrounding the target location to solidify an opening at the target location. In certain embodiments, delivering energy through the slicing element 700A-C helps slice through target tissue during shunting. In certain embodiments, delivering energy through the slicing element 700A-C helps prevent tissue regrowth around the created shunt after the procedure.

In some embodiments, the slicing elements 700A-C may utilize energy to create an easier slicing mechanism as well as solidify the shunt geometry post-slicing. In some embodiments, the energy may be dissipated across a larger portion (e.g., a metallic portion) of the slicing element 700A-C. In some embodiments, the energy may be localized to a point (e.g., point 708A or 708B), an edge (e.g., a sharp edge on the slide of the slicer formed by the two sides 702A and 704A), or one or more sides of the slicing element 700A-C. In some embodiments, the energy may be localized to blunt ends (e.g., blunt ends 710A or 710B) of the slicing element 700A-C.

The cross-sectional shapes of the slicing element 700A-C may vary greatly depending on desired sharpness and surface area contact with the blunt ends (e.g., 710A or 710B). In some embodiments, the sharpness of a puncture element may vary based on a curvature from the blunt ends (e.g., 710A or 710B) to a point on the slicer (e.g., point 708A or 708B). This curvature may be a straight line connecting the two points or can also be a curved radius.

FIGS. 8A-C are schematic diagrams of side view of an example of a slicing element 800A-C, in accordance with embodiments of the present disclosure. As shown in FIG. 8A, the slicing element 800A includes a puncture element 814 and a slicer 808A. In some embodiments, the slicer 808A includes a serrated edge 802A having a length (l1) of from about 7 mm to about 25 mm. In certain embodiments, the serrated edge 802A may span the entire length of the slicer 808A. The serrated edge 802A may be jagged, including a plurality of sharp protruding points.

As shown in FIG. 8B, the slicing element 800B includes a puncture element 814 and a slicer 808B. In some embodiments, the slicer 808A includes a serrated edge 802A having a length (l2) of from about 5 mm to about 20 mm. In certain embodiments, the serrated edge 802B may span only part of the length of the slicer 808B.

As shown in FIG. 8C, the slicing element 800C includes a puncture element 814 and a slicer 808C. In some embodiments, the slicer 808C includes a serrated edge 802C having a length (l3) of from about 7 mm to about 25 mm. In certain embodiments, the serrated edge 802C may span only part of the length of the slicer 808C. In certain embodiments, the serrated edge 802C may span the entire length of the slicer 808C. As shown, for example, the serrated edge 802C has a different shape from the serrated edges 802A and 802B. In some embodiments, the serrated edge 802C maybe notched, including a plurality of blunt protruding parts.

FIG. 9A are schematic diagrams of a side view of an example of a slicing element 900 including a slicer 910, a distal end 912, and a puncture element 914, in accordance with embodiments of the present disclosure. FIGS. 9B-9C are cross-sectional views of the slicing element 900, viewed at points B, C, and D along an axis 907 defined along the length of the slicing element 900.

According to some embodiments, the slicing element 900 is tapered along the axis 907 having a first cross sectional area at a first position (e.g., position B) and a second cross sectional area at a second position (e.g., position C). The slicing element 900 may further include a third cross sectional area at a third position (e.g., position D). As shown, the first position B is closer to the distal end 912 of the slicing element than the second position C, and the second position C is closer to the distal end 912 of the slicing element than the third position D.

In some embodiments, for example as viewed from point B, the slicing element 900 has a cross-sectional shape including a first side 902B, a second side 904B, an arc 906B, and a slicing tip 908B. The width (WB) measured from the slicing tip 908B to the edge of the arc 906B may be from about 2 mm to about 2.5 mm.

In some embodiments, for example as viewed from point C, the slicing element 900 has a cross-sectional shape including a first side 902C, a second side 904C, an arc 906C, and a slicing tip 908C. The width ($W_C$) measured from the slicing tip 908C to the edge of the arc 906C may be from about 1.5 mm to about 2 mm.

In some embodiments, for example as viewed from point D, the slicing element 900 has a cross-sectional shape including a first side 902D, a second side 904D, an arc 906D, and a slicing tip 908D. The width ($W_D$) measured from the slicing tip 908D to the edge of the arc 906D may be from about 1 mm to about 1.5 mm.

In certain embodiments, the first cross sectional area of the slicing element 900 (e.g., as shown in FIG. 9B) is greater than the second cross sectional area of the slicing element 900 (e.g., as shown in FIG. 9C). In certain embodiments, the second cross sectional area of the slicing element 900 (e.g., as shown in FIG. 9C) is greater than the third cross sectional area of the slicing element 900 (as shown in FIG. 9D).

In certain embodiments, the tapered slicing element 900 including different cross sectional areas along the axis 907 is more hemodynamic during slicing. In some instances, the different cross sectional areas along the axis 907 creates an angle on the slicer 910 such that the slicing is more energy efficient. In certain instances, the different cross sectional areas along the axis 907 are configured such that when slicing through a vessel wall, the opening may be bigger on one side of the vessel wall and smaller on the opposite side of the vessel wall. For example, after the puncture element 914 punctures through a vessel wall between a patient's CS and LA, the tapered slicer 910 may be used to slice through the vessel wall to create an opening bigger on the LA side and smaller on the CS side. In some examples, the hemodynamic pressure in a patient's LA may be larger than the pressure in the patient's CS.

FIGS. 10A-10D are schematic diagrams of perspective views of an example of a slicing element 1000, in accordance with embodiments of the present disclosure. As shown, the slicing element 1000 includes a distal end 1002, a proximal end 1004, a slicer 1008, a backside 1006 on the opposite side of the slicer 1008, and a puncture element 1014. In some embodiments, the slicing element 1000 includes a cavity 1030 along the length of the slicing element 1000. In some embodiments, the slicing element 1000 includes an opening 1032 located on the backside 1006 close to the distal end 1002 of the slicing element 1000. In certain embodiments, the cavity 1030 may be elongated in shape, and connected to the opening 1032.

Figure 10A:
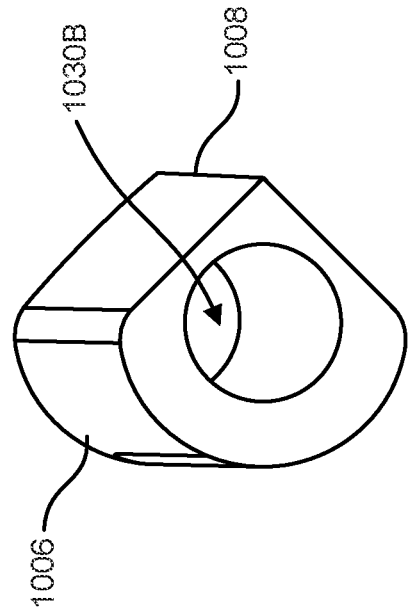
FIGS. 10A-10D are schematic diagrams of perspective views of an example of a slicing element, in accordance with embodiments of the present disclosure.
Figure 10B:
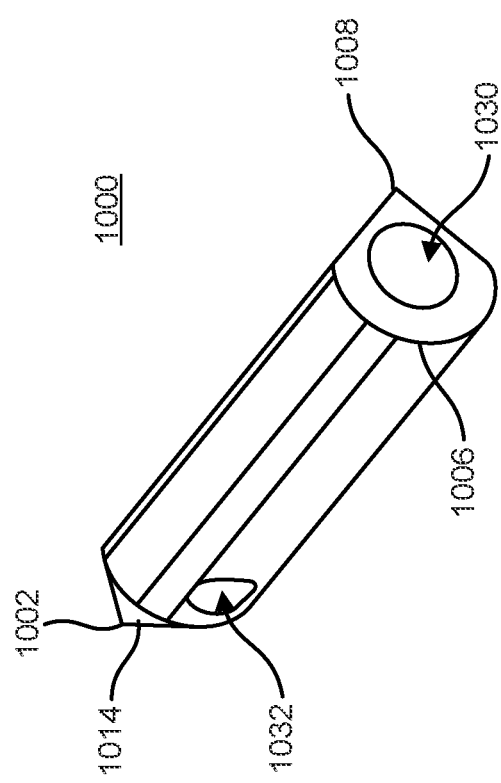
Figure 10C:
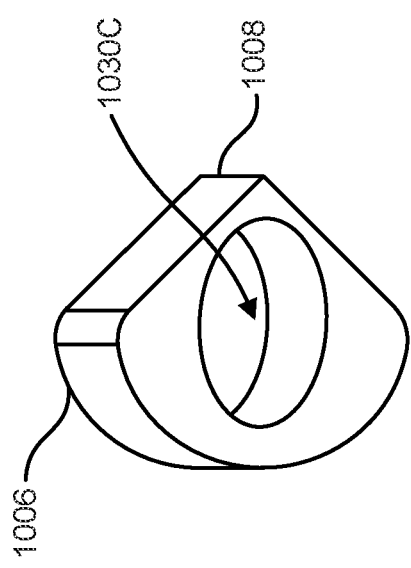
Figure 10D:
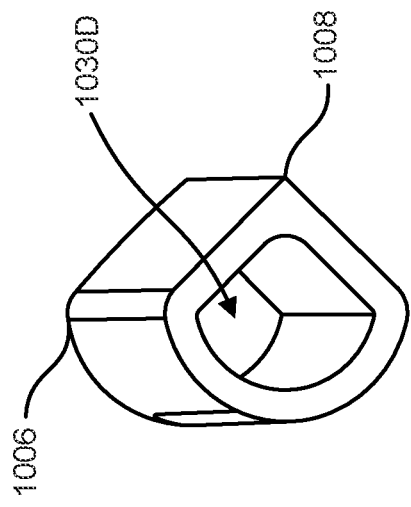

According to some embodiments, for example as shown in FIGS. 10B-10D, the cavity 1030 includes a plurality of different cross-sectional shapes (e.g., circular, oval, or a shape conforming to the shape of the slicing element 1000). In certain embodiment, the cavity 1030 has a shape conforming to the shape of the slicing element 1000. In some embodiments, a slicing element 1000 having one or more cavities may be easier to move, and thus more energy efficient when slicing through a vessel wall.

In certain embodiments, for example when puncturing through a vessel wall using the puncture element 1014, blood may flow from one side of the wall (e.g., from the opening 1032) to the other side of the wall (e.g., through the cavity 1030), indicating that the puncture element 1014 has penetrated through the wall. For example, when puncturing through a wall between a patient's CS and LA, the opening 1032 and/or cavity 1030 may serve as a port for blood to aspirate from the LA to the CS, indicating location of the puncture element 1014 relative to the patient's LA.

In some embodiments, the cavity 1030 may be used as a pathway for supplying cooling agent (e.g., chilled saline) to heal tissue surrounding the target location. In some embodiments, the cavity 1030 may be used as a pathway for containing contrast dye to indicate location of the slicing element 1000 within a patient's CS and/or LA. In certain instances (not shown), the slicing element may include a cavity on the slicer 1008, opposite the backside 1006.

FIGS. 11A-C are schematic diagrams of side views of an example of a shunting catheter 1100, according to certain embodiments of the present disclosure. FIGS. 11A-C are merely examples. One of the ordinary skilled in the art would recognize many variations, alternatives, and modifications. As shown, the shunting catheter 1100 includes a catheter shaft 1104 and a slicing element 1106A-C.

In some embodiments, the slicing element 1106A-C is disposed within the catheter shaft 1104 at a first state (e.g., during deployment, during deployment to position the slicing element 1106A-C). In some embodiments, the slicing element 1106A-C is extended from the catheter shaft 1104 at a second state (e.g., during shunting/slicing).

According to certain embodiments, the shunting catheter 1100 includes an apposition element 1108 configured to be disposed within the 1104 at a first state (e.g., during deployment), and protrudes from the catheter shaft 402 at a second state (e.g., during shunting/slicing). According to some embodiments, for example during the tracking of the shunting catheter 1100 to a target location in a patient's CS, the slicing element 1106A-C may be translated out of the catheter shaft 1104 to puncture a target location on a wall 1110 (e.g., a vessel wall between a patient's CS and LA). In embodiments, the apposition element 1108 is made of a flexible material and configured to appose a vessel a wall 1110 (e.g., a vessel wall between a patient's CS and LA) during shunting. In some embodiments, the apposition element 1108 provides stability to the shunting catheter 1100 during deployment and/or shunting.

In some embodiments, the slicing element 1106A-C includes a slicing element shaft 1112 having a predetermined curve for the slicing element to deploy, a puncture element 1114, a slicer 1116, and a mechanical indicator 1120. The slicing element 1106A-B may have a telescoping feature (e.g., puncture element 1114 is retractable into the slicing element shaft 1112) to allow for the blunt end of the slicing element shaft 1112 to contact a vessel before the puncture element 1114 is translated forward to make contact with the wall. In embodiments, the telescoping feature of the slicing element 1106A-B allows for a safe delivery of the puncture element 1114 to the target location.

In some embodiments, for example as shown in FIG. 11A, the slicing element 1106A has a first deployed state where the slicing element 1106A is extended from the catheter shaft 1104, and the puncture element 1114, the slicer 1116, and the mechanical indicator 1120 are all retracted and crimped inside the slicing element shaft 1112. As shown, the distal end of the slicing element 1106A is blunt during the first deployment state, such that if adjustment of position is needed, the vessel wall surrounding the target location would only make contact with a blunt surface of the slicing element 1106A.

In some embodiments, for example as shown in FIG. 11B, the slicing element 1106B has a second deployed state where the slicing element 1106B is extended from the catheter shaft 1104, and the puncture element 1114, the slicer 1116, and the mechanical indicator 1120 are all protruded from the slicing element shaft 1112. In certain instances, for example during slicing, the shunting catheter 1100 moves in a translational direction indicated by arrow 1118B to create a shunt at the target location. In embodiments, the puncture element 1114, the slicer 1116, and the mechanical indicator 1120 all maintain their relative position to the shunting catheter 1100 during slicing.

In some instances, for example as shown in FIG. 11C, the slicing element 1106C moves in a translational direction indicated by arrow 1118C to create a shunt at the target location. In embodiments, the puncture element 1114, the slicer 1116, and the mechanical indicator 1120 all move along with the slicing element 1106C, whereas the catheter shaft 1104 remains still.

According to certain embodiments, the slicing element 1106A of the shunting catheter 1100 has a first deployment state (e.g., shown in FIG. 11A) and a second deployment state (e.g., shown in FIGS. 11B-C). In some embodiments, the puncture element 1114 is retracted in a cavity of the slicing element shaft 1112 at the first deployed state. In some embodiments, the puncture element 1114 is extended from a distal end of the slicing element shaft 1112 at the second deployed state. In certain embodiments, for example at the second deployment state (e.g., during slicing), the entire shunting catheter 1100 moves in a translational direction to slice through a wall (e.g., a vessel wall between a patient's CS and LA). In certain embodiments, for example at the second deployment state (e.g., during slicing), the only part moving is the slicing element (e.g., slicing element 1118C) in a translational direction to create a shunt, whereas the other parts of the shunting catheter (e.g., the catheter shaft 1104) remains still.

In some embodiments, the mechanical indicator 1120 may take on various geometric shapes including, but not limited to, a uniform bowl shape or two tabs that are radiopaque under fluoroscopy. In some embodiments, the mechanical indicator 1120 has high density radiopaque markers either weaved into a braid or is attached onto the mechanical indicator 1120. The radiopaque marker may include materials including, for example, gold, tantalum, platinum, nickel-titanium-platinum alloy, bismuth, iodine, barium, and/or a combination thereof. In some embodiments, the mechanical indicator 1120 may also serve as a mechanical stop to ensure the slicing element 1106A-C is not protruding further into the patient's LA than intended.

In certain embodiments, the shunting catheter 1100 includes a lumen 1102 disposed on the outside and surrounding the catheter shaft 1104. In some instances, the lumen 1102 is configured to control expansion of the apposition element 1108. The lumen 1102 may be further disposed inside an outer shaft (not shown).

In some embodiments, shunting catheter 1100 further includes an additional lumen disposed between the catheter shaft 1104 and the slicing element shaft 1112. After the slicing element 1106A is positioned at a target location, for example as shown in FIG. 11A, the additional lumen may be pulled back to deploy the crimped puncture element 1114, the slicer 1116, and the mechanical indicator 1120.

In some embodiments, the shunting catheter 1100 includes multiple compartments (e.g., lumens) for various elements to provide more targeted control during deployment. For example, besides the lumen 1102 and/or the additional lumen to control deployment of the slicing element, the shunting catheter 1100 may include additional one or more additional lumens for separately containing functional components such as a guidewire or pull wire assembly. In some examples, the shunting catheter 1100 may include additional lumens for holding shunted tissue from a vessel wall.

Figure 12B:
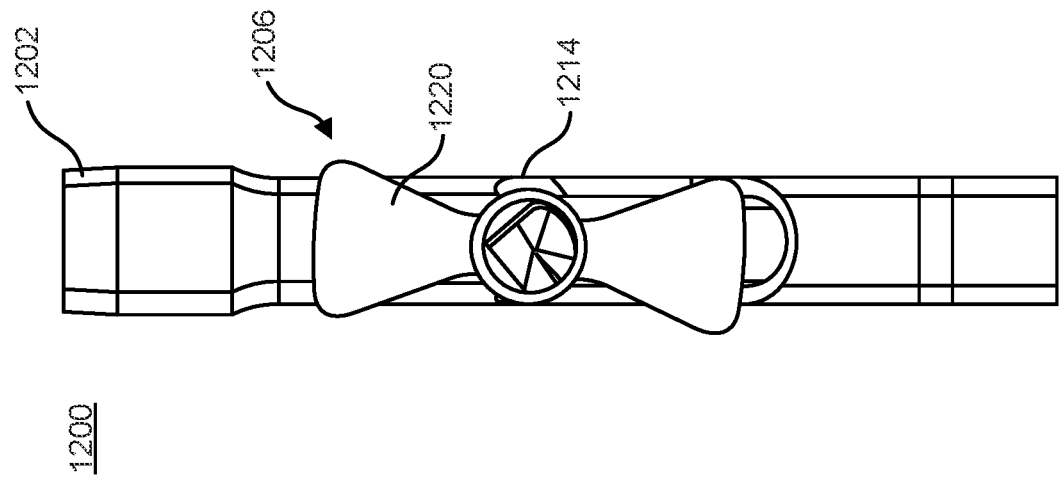
FIGS. 12A-12B are schematic diagrams of a perspective view and a top view of an example of a shunting catheter including a mechanical indicator, according to certain embodiments of the present disclosure.
Figure 12A:
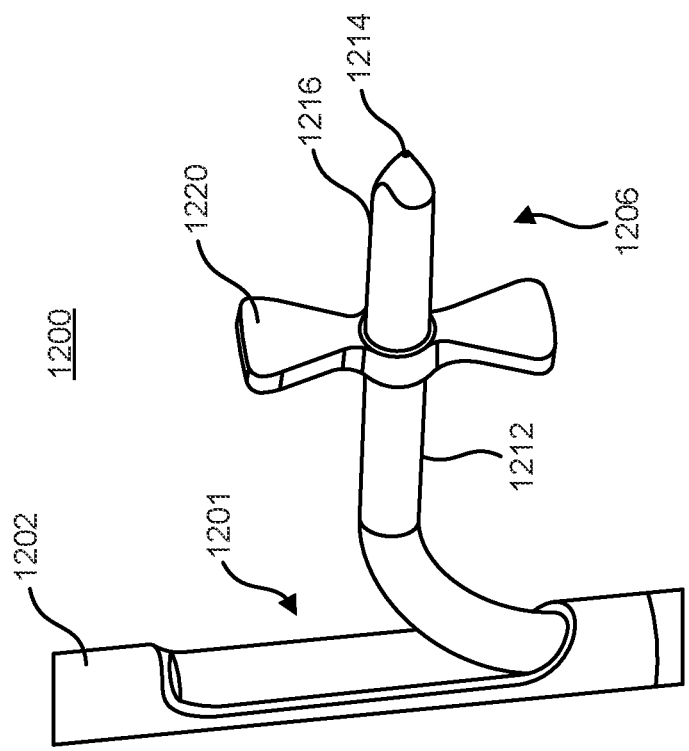

FIGS. 12A-B are schematic diagrams of a perspective view and a top view of an example of shunting catheter 1200 including a mechanical indicator 1220, according to certain embodiments of the present disclosure. FIGS. 12A-B are merely examples. One of the ordinary skilled in the art would recognize many variations, alternatives, and modifications. As shown, the shunting catheter 1200 includes a catheter shaft 1202 having a shaft opening 1201 and a slicing element 1206 disposed within the catheter shaft 1202 at a first state (e.g., during deployment, during deployment to position of the slicing element 1206). In some embodiments, the slicing element 1206 is extended from the catheter shaft 1202 at a second state (e.g., during shunting/slicing).

As shown, the slicing element 1206 includes a puncture element 1214, a slicer 1216, and a mechanical indicator 1220. In some embodiments, the mechanical indicator 1220 is protruded from the slicing element shaft 1212 in a direction generally perpendicular to the slicing element shaft 1212.

In some embodiments, the mechanical indicator 1220 may take on various geometric shapes. In some instances, for example as shown in FIG. 12A, the mechanical indicator 1220 includes two tabs. In certain instances, the two tabs may be radiopaque under fluoroscopy to indicate a location of the slicing element 1206 during deployment. In some embodiments, the mechanical indicator 1220 has a generally flat outer surface.

In some embodiments, the mechanical indicator 1220 has high density radiopaque markers either weaved into a braid or is attached onto the mechanical indicator 1220. The radiopaque marker may include materials including, for example, gold, tantalum, platinum, nickel-titanium-platinum alloy, bismuth, iodine, barium, and/or a combination thereof. In some embodiments, for example when puncturing through a wall between a patient's CS and LA with the puncture element 1214, the mechanical indicator 1220 may serve as a mechanical stop to ensure the slicing element 1206 is not protruding further into the patient's LA than intended.

In certain embodiments, for example during slicing, the mechanical indicator may be located on the CS side of a wall between a patient's CS and LA. In certain embodiments, for example during slicing, the mechanical indicator may be located on the LA side of a wall between a patient's CS and LA.

Figure 13:
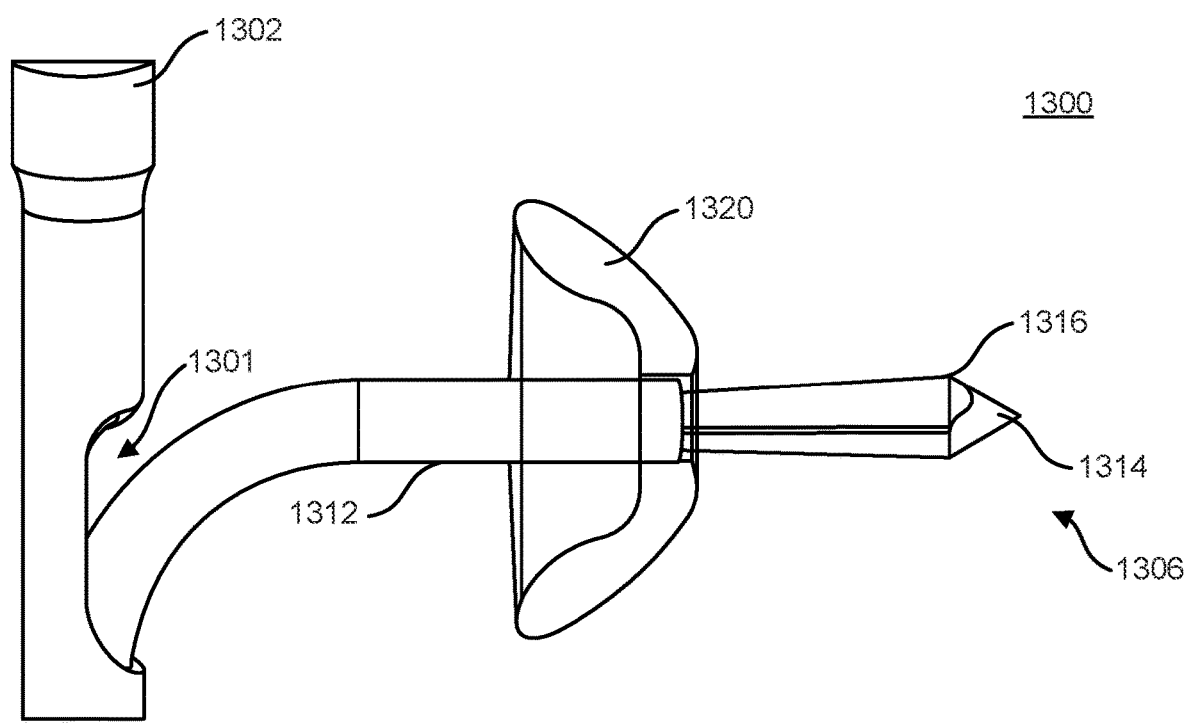
FIG. 13 is a schematic diagram of a side view of an example of a slicing element including a mechanical indicator, according to certain embodiments of the present disclosure.

FIG. 13 is a schematic diagram of a side view of an example of a slicing element, according to certain embodiments of the present disclosure. FIG. 13 is merely an example. One of the ordinary skilled in the art would recognize many variations, alternatives, and modifications. As shown, the shunting catheter 1300 includes a catheter shaft 1302 having a shaft opening 1301 and a slicing element 1306 disposed within the catheter shaft 1302 at a first state (e.g., during deployment, during deployment to position of the slicing element 1306). In some embodiments, the slicing element 1306 is extended from the catheter shaft 1302 at a second state (e.g., during shunting/slicing).

As shown, the slicing element 1306 includes a puncture element 1314, a slicer 1316, and a mechanical indicator 1320. In some embodiments, the mechanical indicator 1320 is protruded from the slicing element shaft 1312 in a direction generally perpendicular to the slicing element shaft 1312.

In some embodiments, the mechanical indicator 1320 may take on various geometric shapes. In some instances, for example as shown in FIG. 13, the mechanical indicator 1320 has a uniform bowl shape. Having a bowl shape may allow the mechanical indicator 1320 to conform better to the slicing element shaft 1312 when the mechanical indicator 1320 is crimped within the shaft 1312 at a first state. In certain instances, the mechanical indicator 1320 having a bowl shape may be radiopaque under fluoroscopy to indicate a location of the slicing element 1306 during deployment. In some instances, the mechanical indicator 1320 has a bowl shape where the inside of the bowl is facing in a direction of puncturing to help crimping the mechanical indicator 1320 inside the shaft 1312 and/or better contact a vessel wall. In some instances, the mechanical indicator 1320 has a bowl shape where the inside of the bowl is facing in a direction opposite of puncturing to better conform to the shape of a vessel wall upon deployment.

In certain embodiments, the mechanical indicator 1320 may be braided. In some embodiments, the mechanical indicator 1320 is made of a flexible material (e.g., nitinol) to help with compressibility into the slicing element shaft 1312. In certain embodiments, the mechanical indicator 1320 has an arc outer surface, for example, confirming to a cardiovascular wall (e.g., a saddle shape, etc.).

In some embodiments, the mechanical indicator 1320 has a high density radiopaque markers either weaved into a braid or is attached onto the mechanical indicator 1320. The radiopaque marker may include materials including, for example, gold, tantalum, platinum, nickel-titanium-platinum alloy, bismuth, iodine, barium, and/or a combination thereof. In some embodiments, for example when puncturing through a wall between a patient's CS and LA with the puncture element 1314, the mechanical indicator 1320 may serve as a mechanical stop to ensure the slicing element 1306 is not protruding further into the patient's LA than intended.

In certain embodiments, for example during slicing, the mechanical indicator may be located on the CS side of a wall between a patient's CS and LA. In certain embodiments, for example during slicing, the mechanical indicator may be located on the LA side of a wall between a patient's CS and LA.

Figure 14:
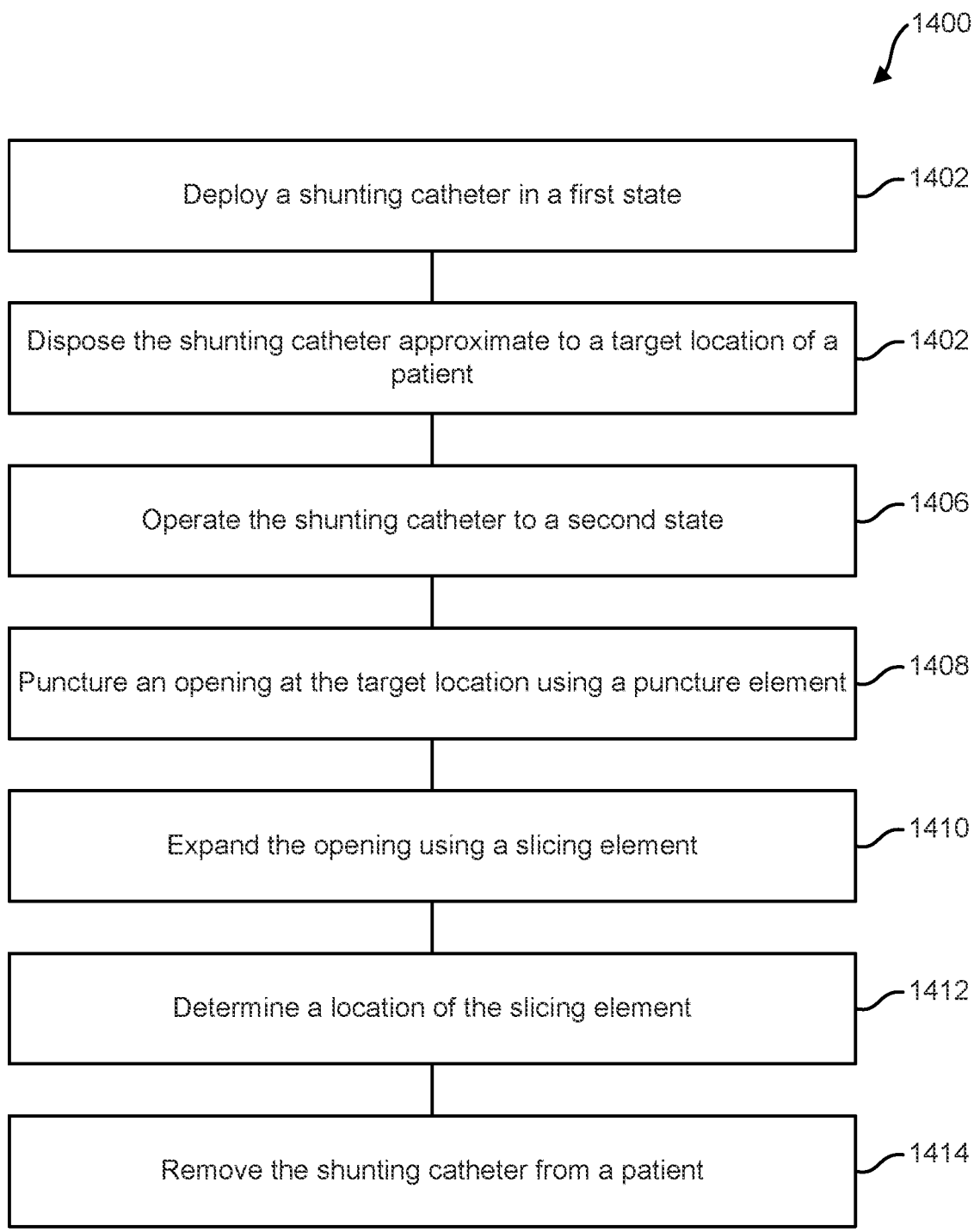
FIG. 14 is a flow diagram illustrating an example process of creating a shunt in a patient, in accordance with embodiments of the present disclosure.

FIG. 14 is a flow diagram illustrating an example process 1400 of creating a shunt in a patient, in accordance with embodiments of the present disclosure. Aspects of embodiments of the method may be performed, for example, by a shunting catheter system or a controller (e.g., the system 104 in FIG. 1, the controller 112 in FIG. 1). One or more steps of method are optional and/or can be modified by one or more steps of other embodiments described herein. Additionally, one or more steps of other embodiments described herein may be added to the method. In some embodiments, the shunt may be formed in a coronary sinus of a patient. In certain embodiments, the shunt includes an opening between a patient's coronary sinus and left atrium.

At step 1402, the process 1400 includes deploying a shunting catheter in a first state, the shunting catheter including a catheter shaft including a shaft lumen and a slicing element disposed in the shaft lumen at a first state. In some embodiments, the slicing element includes a slicing element shaft, a puncture element, and a slicer. In some embodiments, the slicing element is disposed in the shaft lumen at the first state. In certain embodiments, the catheter shaft has a shaft opening, and the slicing element extends from the catheter shaft through the shaft opening. In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1404, the process 1400 includes disposing the shunting catheter approximate to a target location of a patient. At step 1406, the process 1400 includes operating the shunting catheter to a second state, wherein the slicing element extends from the catheter shaft at an angle greater than zero degree at the proximal end of the slicing element at the second state. In some embodiments, the shunting catheter includes an apposition element disposed proximate to the slicing element, and the apposition element is protruded from the catheter shaft at the second state.

At step 1408, the process 1400 includes puncturing, using the puncture element, an opening at the target location. In some embodiments, the target location is at a coronary sinus of a patient. In some embodiments, the slicing element includes a cavity. In certain embodiments, the slicing element has a first deployed state and a second deployed state, and the puncture element is retracted in the cavity of the sliding element at the first deployed state. In certain embodiments, the puncture element is extended from the slicer at the distal end at the second deployed state. In some instances, the process 1400 may include stabilizing the slicing element during the second state, and before puncturing the opening at the target location.

At step 1410, the process 1400 includes expanding the opening using the slicing element. In some embodiments, expanding the opening includes slicing through tissue surrounding the target location via translational movement of the shunting catheter. In some embodiments, expanding the opening includes slicing through tissue surrounding the target location via translational movement of the slicing element without moving the other parts of the shunting catheter. In certain embodiments, the catheter shaft has a shaft opening, and the slicing element extends from the catheter shaft through the shaft opening. In some instances, the slicing element is configured to deliver energy (e.g., ablative energy, radiofrequency (RF) energy, thermal energy, pulse ablative energy, microwave, laser, etc.) when slicing to expand the opening.

At step 1412, the process 1400 includes determining a location of the slicing element. In some embodiments, determining a location of the slicing element includes using a imaging device with one or more visualization elements disposed proximate the slicing element.

In some embodiments, the slicing element may include a mechanical indicator having high density radiopaque markers either weaved into a braid or is attached onto the mechanical indicator. The radiopaque marker may include materials including, for example, gold, tantalum, platinum, nickel-titanium-platinum alloy, bismuth, iodine, barium, and/or a combination thereof. In some embodiments, determining a location of the slicing element may involve use of the mechanical indicator with radiopaque markers. In certain embodiments, the mechanical indicator may also serve as a mechanical stop to ensure the slicing element is not protruding further than intended (e.g., into a patient's LA if the puncture element is used to puncture through a wall between a patient's CS and LA).

In some embodiments, the slicing element includes a center cavity (e.g., cavity 1030 in FIG. 10A) filled with used as a pathway for containing contrast dye. The determining a location of the slicing element may involve using the contrast dye in a center cavity of the slicing element to indicate location of the slicing element.

At step 1414, the process 1400 includes removing the shunting catheter from a patient. In some embodiments, the process 1400 may include removing the shunting catheter, which includes removing the catheter shaft, the puncture element, and the slicing element. In certain embodiments, the process 1400 does not leave any implant device at the target location. In some embodiments, a shunt is formed by creating an opening between a coronary sinus and a left atrium of a patient. In certain embodiments, the shunting catheter is removed from the coronary sinus of the patient. In certain embodiments, the formed shunt is an opening that does not include an implant (e.g., a frame or structure to support an opening). In some embodiments, the shunt includes an opening between the coronary sinus and the left atrium of a patient, where the shunt does not include an implant.

According to some embodiments, the process 1400 includes generating a shunt using a slicing element of a shunting catheter. In certain embodiments, the shunt includes an expanded opening between the coronary sinus and left atrium of a patient. In some embodiments, the shunt does not include any implant.

According to some embodiments, a shunting catheter includes: a catheter shaft including a shaft lumen; and a slicing element including a distal end and a proximal end, and including a slicing element shaft, a puncture element, and a slicer; the slicing element is disposed in the shaft lumen at a first state; the slicing element is extended from the catheter shaft at the proximal end of the slicing element at a second state; and the puncture element is disposed at the distal end of the slicing element.

According to certain embodiments, the catheter shaft has a shaft opening, and the slicing element extends from the catheter shaft through the shaft opening.

According to some embodiments, the catheter shaft includes a distal end and a proximal end, and the shaft opening is not at the distal end of the catheter shaft.

According to certain embodiments, a portion of the catheter shaft between the shaft opening and the distal end of the catheter shaft has a curve.

According to some embodiments, the catheter shaft defines a first axis, the slicing element defines a second axis at the second state, and the second axis and the first axis form an angle greater than zero degree.

According to certain embodiments, the angle is greater than 10 degrees.

According to some embodiments, the slicer of the slicing element has a circular cross-sectional shape; and the slicing element is configured to deliver energy to a target tissue.

According to certain embodiments, the energy delivered by the slicing element includes at least one selected from a group consisting of ablative energy, radiofrequency (RF) energy, phased RF energy, thermal energy, pulse energy, microwave energy, laser energy, and ultrasonic energy.

According to some embodiments, the slicer of the slicing element has a cross-sectional shape generally perpendicular to the second axis, the cross-sectional shape includes two sides and an arc, and the two sides of the cross-sectional shape form an angle less than 90 degrees.

According to certain embodiments, at least one of the two sides is a curve.

According to some embodiments, both of the two sides are curves, and the two sides form a sharp edge.

According to certain embodiments, the slicer includes a serrated edge along the second axis.

According to some embodiments, the slicing element further includes a mechanical indicator protruded from the slicing element shaft.

According to certain embodiments, the mechanical indicator has an arc outer shape.

According to some embodiments, the slicing element includes a cavity.

According to certain embodiments, the slicing element has a first deployed state and a second deployed state, the puncture element is retracted in the cavity of the slicing element at the first deployed state, and the puncture element is extended from the slicer at the distal end at the second deployed state.

According to some embodiments, the slicer is tapered along the second axis, the slicer has a first cross sectional area at a first position and a second cross sectional area at a second position, the first position is closer to the distal end of the slicing element than the second position, and the first cross sectional area is greater than the second cross sectional area.

According to certain embodiments, the slicing element has a diameter in the range of two millimeters to five millimeters.

According to some embodiments, a method for creating a shunt includes: deploying a shunting catheter in a first state, the shunting catheter including: a catheter shaft including a shaft lumen; a slicing element disposed in the shaft lumen at the first state, the slicing element including a slicing element shaft, a puncture element, and a slicer; disposing the shunting catheter approximate to a target location of a patient; operating the shunting catheter to a second state, and the slicing element extends from the catheter shaft at an angle greater than zero degree at the proximal end of the slicing element at the second state; puncturing, using the puncture element, an opening at the target location; and expanding the opening using the slicing element.

According to some embodiments, the slicing element includes a cavity, the slicing element has a first deployed state and a second deployed state, the puncture element is retracted in the cavity of the slicing element at the first deployed state, and the puncture element is extended from the slicer at the distal end at the second deployed state.

According to certain embodiments, the target location is at a coronary sinus of the patient.

According to some embodiments, deploying the shunting catheter in the first state includes inserting the shunting catheter through a superior vena cava or an inferior vena cava of the patient into a coronary sinus of the patient.

According to certain embodiments, the method further includes removing the shunting catheter from the patient.

According to some embodiments, the method further includes generating the shunt using the slicing element, and the shunt includes the expanded opening between the coronary sinus and a left atrium of the patient.

According to certain embodiments, the shunt does not include any implant.

According to some embodiments, the expanding the opening includes slicing through tissue surrounding the target location via at least one of translational movement, rotational movement, and bending movement of the catheter shaft.

According to certain embodiments, the method further includes stabilizing the slicing element during the second state, and before puncturing the opening at the target location.

According to some embodiments, a shunting catheter system includes: a shunting catheter including: a catheter shaft including a shaft lumen; and a slicing element disposed in the shaft lumen at a first state, the slicing element including a slicing element shaft, a puncture element, and a slicer; an energy source connected to the shunting catheter; and a controller connected to the energy source including one or more processors; the one or more processors are configured to control the energy source to deliver energy to the shunting catheter; and the slicing element is extended from the catheter shaft at the proximal end of the slicing element at a second state.

According to some embodiments, the system further includes an imaging device including: one or more visualization elements disposed proximate the slicing element for determining a location of the slicing element within a heart of a patient, and a display for visualizing the location.

According to some embodiments, a method for creating a shunt, including: deploying a shunting catheter in a first state, the shunting catheter including: a catheter shaft including a shaft lumen; a slicing element disposed in the shaft lumen at the first state, the slicing element including a slicing element shaft, a puncture element, and a slicer; disposing the shunting catheter approximate to a target location of a patient; operating the shunting catheter to a second state, wherein the slicing element extends from the catheter shaft at the second state; and delivering energy from an energy source to the shunting catheter.

Various modifications and additions can be made to the exemplary embodiments discussed without departing from the scope of the present disclosure. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A shunting catheter, comprising:
a catheter shaft including a shaft lumen; and
a slicing element including a distal end and a proximal end, and comprising a slicing element shaft, a puncture element, and a slicer;
wherein the slicing element is disposed in the shaft lumen at a first state;
wherein the slicing element is extended from the catheter shaft at the proximal end of the slicing element at a second state;
wherein the puncture element is disposed at the distal end of the slicing element;
wherein the slicing element further comprises a mechanical indicator protruded from the slicing element shaft;
wherein the mechanical indicator is configured to act as a mechanical stop for the slicing element by contacting tissue of a patient at the second state.

2. The shunting catheter of claim 1, wherein the catheter shaft has a shaft opening, wherein the slicing element extends from the catheter shaft through the shaft opening.

3. The shunting catheter of claim 2, wherein the catheter shaft includes a distal end and a proximal end; wherein the shaft opening is not at the distal end of the catheter shaft.

4. The shunting catheter of claim 3, wherein a portion of the catheter shaft between the shaft opening and the distal end of the catheter shaft has a curve.

5. The shunting catheter of claim 1, wherein the catheter shaft defines a first axis; wherein the slicing element defines a second axis at the second state; wherein the second axis and the first axis form an angle greater than zero degree.

6. The shunting catheter of claim 5, wherein the angle is greater than 10 degrees.

7. The shunting catheter of claim 5, wherein the slicer of the slicing element has a cross-sectional shape generally perpendicular to the second axis;
wherein the cross-sectional shape includes two sides and an arc; and
wherein the two sides of the cross-sectional shape form an angle less than 90 degrees.

8. The shunting catheter of claim 7, wherein at least one of the two sides is a curve.

9. The shunting catheter of claim 7, wherein both of the two sides are curves; wherein the two sides form a sharp edge.

10. The shunting catheter of claim 5, wherein the slicer includes a serrated edge along the second axis.

11. The shunting catheter of claim 5, wherein the slicer is tapered along the second axis;
wherein the slicer has a first cross sectional area at a first position and a second cross sectional area at a second position;
wherein the first position is closer to the distal end of the slicing element than the second position; and
wherein the first cross sectional area is greater than the second cross sectional area.

12. The shunting catheter of claim 1, wherein the slicer of the slicing element has a circular cross-sectional shape; wherein the slicing element is configured to deliver energy to a target tissue.

13. The shunting catheter of claim 12, wherein the energy delivered by the slicing element comprises at least one selected from a group consisting of ablative energy, radiofrequency (RF) energy, phased RF energy, thermal energy, pulse energy, microwave energy, laser energy, and ultrasonic energy.

14. The shunting catheter of claim 1, wherein the mechanical indicator has an arc outer shape.

15. The shunting catheter of claim 1, wherein the slicing element includes a cavity.

16. The shunting catheter of claim 15, wherein the slicing element has a first deployed state and a second deployed state;
wherein the puncture element is retracted in the cavity of the slicing element at the first deployed state; and
wherein the puncture element is extended from the slicer at the distal end at the second deployed state.

17. The shunting catheter of claim 1, wherein the slicing element has a diameter in the range of two millimeters to five millimeters.

18. The shunting catheter of claim 1, wherein the mechanical indicator includes two tabs extending away from the slicing element shaft.

19. A method for creating a shunt, comprising:
deploying a shunting catheter in a first state, the shunting catheter comprising:
a catheter shaft including a shaft lumen;
a slicing element disposed in the shaft lumen at the first state, the slicing element comprising a slicing element shaft, a puncture element disposed at a distal end of the slicing element, and a slicer, and a mechanical indicator protruded from the slicing element shaft;
disposing the shunting catheter approximate to a target location of a patient;
operating the shunting catheter to a second state, wherein the slicing element extends from the catheter shaft at an angle greater than zero degree at the proximal end of the slicing element at a second state;
puncturing, using the puncture element, an opening at the target location; and
expanding the opening using the slicing element; and contacting the mechanical indicator against tissue of the patient such that the mechanical indicator acts as a mechanical stop for the slicing element.

20. The method of claim 19, wherein the slicing element includes a cavity;
wherein the slicing element has a first deployed state and a second deployed state;
wherein the puncture element is retracted in the cavity of the slicing element at the first deployed state; and
wherein the puncture element is extended from the slicer at the distal end at the second deployed state.

21. The method of claim 19, wherein the target location is at a coronary sinus of the patient.

22. The method of claim 19, wherein deploying the shunting catheter in the first state comprises inserting the shunting catheter through a superior vena cava or an inferior vena cava of the patient into a coronary sinus of the patient.

23. The method of claim 19, further comprising: removing the shunting catheter from the patient.

24. The method of claim 19, further comprising:
generating the shunt using the slicing element;
wherein the shunt includes the expanded opening between the coronary sinus and a left atrium of the patient.

25. The method of claim 24, wherein the shunt does not include any implant.

26. The method of claim 24, wherein the expanding the opening comprises slicing through tissue surrounding the target location via at least one of translational movement, rotational movement, and bending movement of the catheter shaft.

27. The method of claim 19, further comprising stabilizing the slicing element during the second state, and before puncturing the opening at the target location.

* * * * *